(12) United States Patent
Post

(10) Patent No.: US 8,393,903 B1
(45) Date of Patent: *Mar. 12, 2013

(54) VIRTUAL WORLD APTITUDE AND INTEREST ASSESSMENT SYSTEM AND METHOD

(71) Applicant: David Post, New York, NY (US)

(72) Inventor: David Post, New York, NY (US)

(73) Assignee: David Post, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/657,713

(22) Filed: Oct. 22, 2012

Related U.S. Application Data

(63) Continuation of application No. 11/979,229, filed on Oct. 31, 2007, now Pat. No. 8,292,626, which is a continuation-in-part of application No. PCT/US2007/003818, filed on Feb. 12, 2007.

(60) Provisional application No. 60/771,881, filed on Feb. 10, 2006.

(51) Int. Cl.
*G09B 19/00* (2006.01)
*G09B 3/00* (2006.01)

(52) U.S. Cl. ......... 434/219; 434/322; 434/323; 434/350

(58) Field of Classification Search .................. 434/219, 434/236, 247, 322, 323, 350
See application file for complete search history.

(56) References Cited

U.S. PATENT DOCUMENTS

| | | |
|---|---|---|
| 6,352,479 B1 | 3/2002 | Sparks, II |
| 7,228,260 B2 | 6/2007 | Fujino et al. |
| 2002/0045154 A1 | 4/2002 | Wood et al. |
| 2002/0072048 A1 | 6/2002 | Slattery et al. |
| 2002/0113809 A1* | 8/2002 | Akazawa et al. ............. 345/706 |
| 2004/0197759 A1 | 10/2004 | Olson |
| 2005/0095569 A1 | 5/2005 | Franklin |
| 2007/0013692 A1* | 1/2007 | Jung et al. ..................... 345/419 |

* cited by examiner

*Primary Examiner* — Xuan Thai
*Assistant Examiner* — Jerry-Daryl Fletcher
(74) *Attorney, Agent, or Firm* — Andrews Kurth LLP; Aldo Noto

(57) ABSTRACT

An aptitude and interest assessment tool identifies one or more sectors for which a user may have a special interest, talent or aptitude. An interactive session is presented to a user. The interactive session provides a virtual world. A user interacts with the virtual world. Some or all of the user's interactions in the virtual world is stored in a storage device. The user's aptitude or interest in a profession or activity is assessed by an assessment module that receives data from the storage device and processes the received data to make a user assessment. A report providing the user assessment is created by a report creator.

20 Claims, 16 Drawing Sheets

Tell us what type of pet you would like?

Answer: ___ ___ ___ ___ ___

|  |  | Black | Tail |
|---|---|---|---|
|  |  | Brown | Hair |
| Dog |  | Grey | Playful |
| Cat | Large | White | Cute |
| Rabbit | Medium | Tan | Well behaved |
| Hamster | Small | Red | Trained |
| Fish |  | Green | Young |
|  |  | Blue | Old |
| Category 1 | Category 2 | Category 3 | Category 4 |
| Type | Size | Color | Other Info. |

VIRTUAL WORLD APTITUDE AND INTEREST ASSESSMENT SYSTEM AND METHOD

REFERENCE TO RELATED APPLICATION

This application claims the benefit of, and incorporates by reference herein in their entirety, U.S. Pat. No. 8,292,626, filed Oct. 31, 2007, as well as U.S. Provisional Application No. 60/771,881, filed Feb. 10, 2006 and a PCT Patent Application Serial No. PCT/US2007/003818 filed Feb. 12, 2007.

FIELD OF THE INVENTION

The invention relates generally to a system and method for assessing a person's aptitude and/or interest in a sector or profession.

BACKGROUND OF THE INVENTION

Parents always want to know if their child has a special talent or aptitude for particular profession. They may see certain traits in the child but may not have the tools to determine whether the child has any hidden talents or aptitude. Even if a parent believes their child has some talent or aptitude, parents want some verification or confirmation as well as guidance on how to nurture or develop the child's talent or aptitude.

In addition, parents may simply want a fun and interesting way to work with their child to develop a particular talent or interest. Since it can be difficult keeping a child occupied or interested, a system that is both fun and educational can be invaluable to parents in determining whether a child has a special talent or aptitude, and to further develop a talent or aptitude.

SUMMARY OF THE INVENTION

An aptitude and interest assessment tool identifies one or more sectors for which a user may have a special interest, talent or aptitude. An interactive session is presented to a user. The interactive session provides a virtual world. A user interacts with the virtual world. Some or all of the user's interactions in the virtual world is stored in a storage device. The user's aptitude or interest in a profession or activity is assessed by an assessment module that receives data from the storage device and processes the received data to make a user assessment. A report providing the user assessment is created by a report creator.

BRIEF DESCRIPTION OF THE DRAWINGS

FIG. 15 illustrates an input interface that may be provided in a AIA system, in accordance with an embodiment.

DETAILED DESCRIPTION

Figure 1:
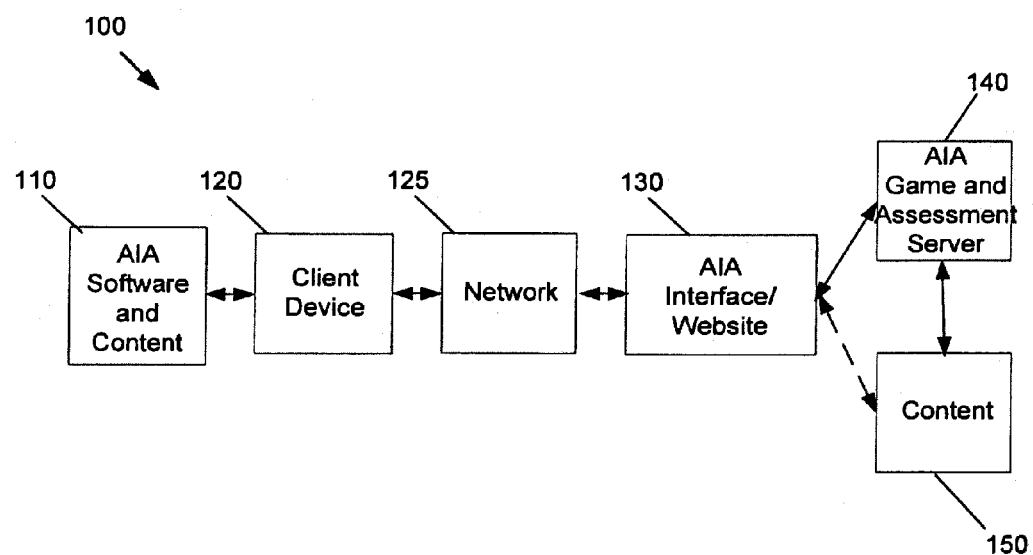
FIG. 1 is diagrammatic representation showing an example of an aptitude and interest assessment (AIA) system.

An Aptitude and Interest Assessment (AIA) system can be used to assess, for example, aptitude, interest, acumen and talent of children and adults towards one or more sectors. As described herein, a sector may include a particular occupation, profession, talent area, field and/or area. The AIA system can be used to discover hidden or unknown talents while providing a fun, entertaining and educational experience.

A parent or other adult can run an AIA on a child to determine whether the child has a particular talent, shows a passion, acumen and/or ability towards a particular sector. As described herein, the AIA system can be used for Acumen and Talent Assessment in Children (ATAC), for example. Of course, the AIA can be performed without supervision by individuals of appropriate age. The AIA may be performed using a virtual world, various types of games including interactive games and question/answer sessions. Virtual world includes but is not limited to (1) single player, (2) massively multiplayer online role-playing games or MMORPGs where the user playing a specific character is a main feature of the game, (3) massively multiplayer online real-life/rogue-like games or MMORLGs, the user can edit and alter their avatar at will, allowing them to play a more dynamic role, or multiple roles.

The games and/or interactive sessions (including virtual worlds) for the AIA, as described herein, may be provided on-line (e.g., via a web-site), on a DVD, CD, downloaded on a personal computer or other device, provided on a gaming station, or a portable game, another type of device or any combination thereof. Although a website, including a virtual world website, may be provided for the AIA, a website is not necessary to implement the AIA.

In one example, the child views a video relating to a particular sector and plays a game to act out a role as a professional in the chosen sector. The sector can be chosen by the parent or child or recommended by the AIA system. The video shown to the child under assessment may include "a day in the life" of an actual person in a particular sector (e.g., I. M. Pei for architecture). The games could be, for example, video games, animations, computer games, virtual world games, board games and/or a combination of games. While the child plays the games the system uses the input from the game to assess the child. The games provide, for example, the child with an experience of what it would be like to be working or performing in the chosen sector or talent area. As one example, the child may take part in a reality game in which the child actually plays the part of an individual in the chosen sector (e.g., doctor, lawyer, architect, construction worker, baseball player, etc.). Thus, the child gets first hand experience of what it would be like to be working in that field. In an embodiment, a virtual world is used and a game or series of games may be presented in which a sector of interest may be explored, and subsequently assessed by the system.

While playing the games, the child may be provided with various obstacles, puzzles, and challenges, relating to the sector, that may change with the child's responses. The child will also be presented with questions that relate to the child's experiences in that role and relate to that sector. For consistency in assessment, the virtual world videos, games or assessment sessions may last for a predetermined fixed period of time. For example, the video may be 5 minutes in duration and the games may be 15 minutes in duration. If the video or game cannot be completed, the child can return to complete and continue the assessment process. Of course, the video and/or games can be of any time duration.

In the AIA system, the virtual world video, games, questions and other interaction with the child are based on the age or skill level of the child. Thus, if the child is, for example, 2 years old, then the video, games, questions will be directed to that age level. Even the technology used for interaction may be directed to the child's age. Older children will be presented with video, games, questions, or interaction technology directed to their age. Thus, the child can comprehend what is being presented and the assessment process will be meaningful. In one example, the AIA system, described herein, (e.g., video content, games, questions or technology) may be directed to children between the ages of 2 to 9. The AIA system can also be directed to younger or older individuals.

The games in the system may be created as 2D flash games, played as 3D games with or without an avatar and/or played as live action video games. The games may connect to the real world, real world situations and/or real world situations may connect to the games. Optionally or additionally, the games may connect to other games so similar attributes may be used by the player and analyzed, and the results can be compared.

During the games, question/answer or interaction sessions, various parameters are measured and recorded along with the child's responses. In addition to measuring correct or incorrect responses, successful completion of a game, obstacle, puzzle, etc., other parameters may be measured and used to measure the child's overall performance and/or performance in a particular category. The categories may include quickness of responses, quickness in completing one or more obstacles, challenges, puzzles or games, the child's reactions, enjoyment level or other parameters may be measured. Some categories may be measured automatically or manually, while other may be measured based on input from the child or parent (e.g., enjoyment level of the game and/or sector). The parameters and responses are processed, as described below, and an output is provided to the parents.

Artificial Intelligence (AI) or similar technologies may be used in all aspects of the AIA system. For example, the AIA system may use AI to interact with the parent/child, process the games, ask questions, request input and/or present output. In addition, AI technologies may be used to recognize, identify and/or process the responses and measured parameters, and to generate a useful and meaningful assessment. The AI technologies include all known and future technologies. AI processes include automated reasoning and machine learning. The AI technologies include, but are not limited to, decision trees, Expert Systems, Fuzzy Logic Natural Language Processing/Understanding, and/or Latent Semantic Analysis (LSA). The AIA system may use one or more of these or other technologies in one or more aspects (e.g., game processing, game play, response analysis, interaction, assessment analysis, result analysis, output, etc.) of the AIA system.

The output may contain information indicating how much the child enjoyed the game, how much the child learned and whether the child has any natural acumen or talent in the sector. The parent may also be provided with other recommendations, for the child, such as joining clubs associated with a particular sector, performing other activities relating to the sector, contacting an expert in that particular sector, viewing recommended programs, and/or running additional assessments.

FIG. 1 is diagrammatic representation showing an example of an AIA system 100. The AIA system 100 includes AIA software and content 110. The AIA software and content 110 may be provided on a CD, DVD or downloaded from an AIA server 140. The AIA software and content 110 may be installed on the client device 120. The client device 120 may be a computer, a PDA, cell phone, interactive television (e.g., IPTV), a television that includes a smart set top box, palm top computer, tablet PC, a mobile device or any other electronic device. The games can be played and/or the assessment process performed, for example, on the client device. The games or interactive sessions may be animated, live action video, virtual world games including avatar play, game engines and/or thought games.

The aptitude, acumen, talent, and/or interest assessment (also referred to herein as "the AIA" or "the assessment") can be preformed using the AIA system 100 and/or on a stand alone client device (e.g., installed with the AIA software and content). The assessment preferably includes providing the video content, the playing and processing of the games, receipt, processing and analysis of the various responses and measured parameters, output of results and recommendations, and/or other features, as described herein. Although the term "aptitude" is used herein, this term may broadly refer to one or more of aptitude, interest, acumen and talent for a particular sector.

The client device 120 may be stand alone or coupled to a network 125. The network 125 is a communications network that includes, for example, a public switched telephone network (PSTN), an Integrated Services Digital Network (ISDN), a cellular network, a digital mobile network, a Personal Communication Systems (PCS) network, an Internet, an intranet, a signaling system 7 (SS7) network, a local area network (LAN), a satellite network, an advance intelligent network (AIN), any suitable digital or analog network, a broadband network such as a cable network, any other suitable national and/or international communications network or any combination thereof.

The network 125 includes a plurality of switches, communication interfaces, and/or other components that are not shown for convenience. The communications provided using the network 125 include hard-line, wireless, RF, optical, or any other type of communications or any combination thereof. The various devices, systems, networks, etc. may be appropriately configured or equipped with hardware and/or software to operate in such environments.

The client device 120, with the AIA software and content 110 installed, is used to access the AIA interface/website 130 via network 125. The AIA interface 130 is provided by AIA game and assessment server 140. As described herein, processing of the interface 130 and interaction with user may occur at the AIA game and assessment server 140 and/or another server (not shown). The AIA game and assessment server 140 may provide the user interfaces, various games, processes the AIA and generates the AIA output, as described herein. As described above, the AIA server 140 may use various techniques such as artificial intelligence (AI) to provide games, generate assessments and provide output. The AIA server 140 accesses content 150. The content 150 may include a virtual world, various game programs and associated game content, video content, question/answer sets, assessment programs, sector information, and/or other information relating to various sectors. The content 150 may be located internal to or external to the AIA server 140.

Figure 2:
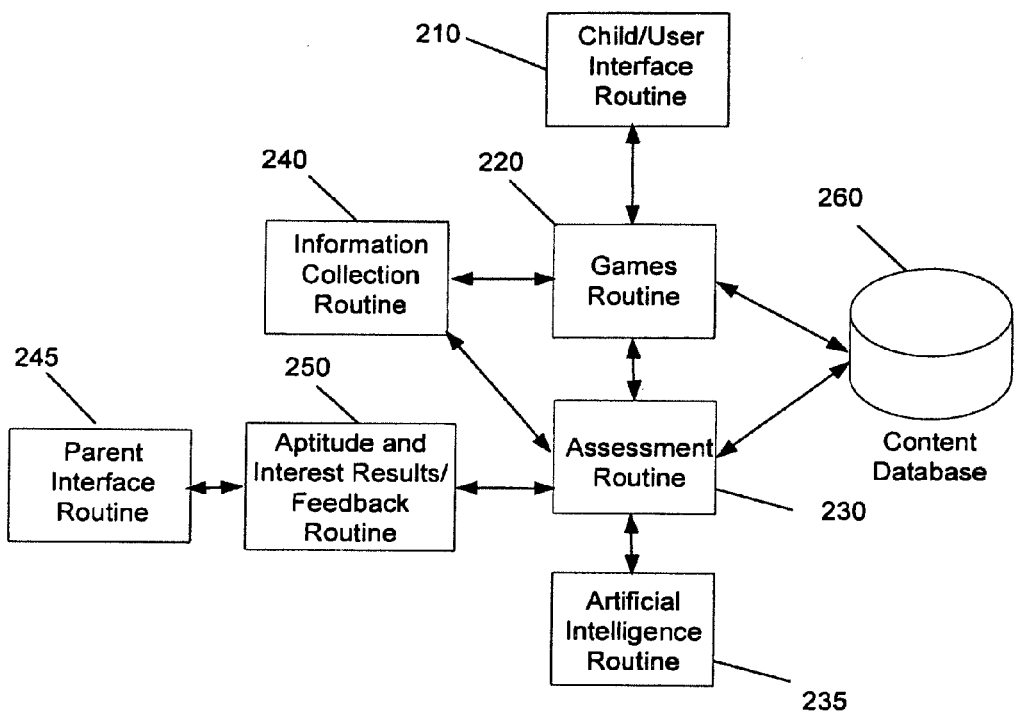
FIG. 2 is diagrammatic representation showing an example of the interaction between various AIA routines and subroutines that may be processed by an MA program.

FIG. 2 is diagrammatic representation showing an example of the interaction between various AIA routines and sub-routines that may be processed by AIA program. The various AIA routines and/or sub-routines may be processed by one or more devices in the MA system 100, for example, the AIA game and assessment server 140, at the client device 120, other locations such as in the network 125, and/or any combination thereof. One or more of the various routines and/or sub-routines, as described herein, may be included in or processed by the AIA software and content 110.

In one example, the various routines may include a child/user interface routine 210 that interfaces with the game routine 220 to provide the interactive games and question/answer sessions to children that are used for AIA purposes. The game routine 220 may provide a virtual world in which the child may practice a sector (occupation, profession, talent area, field and/or area). The game routine 220 receives the user responses from the child interface routine 210 and the responses are collected by the information collection routine 240. The responses include responses to various questions presented during the game and the results of a particular obstacle, challenge, puzzle or objective presented during the game. In this example, the game routine 220 or information collection routine 240 may receive or measure various parameters such as the duration of a game, the amount of time it takes to complete a particular obstacle, challenge, puzzle or objective presented during the game and other information that may be used to determine aptitude or interest associated with a particular sector. The responses and measured parameters are processed by the assessment routine 230 which provides the AIA and generates output providing results of the assessment. The assessment routine may generate a user attribute, as describe herein. The game routine 220 draws information from the content database 260 to generate the various games, questions and other information (e.g., video content, sector information, etc.). The assessment routine 230 may also draw information from the content database 260 to perform the AIA.

An artificial intelligence (AI) routine 235 may also be used in the assessment (and gaming) process and interface with the assessment routine 230, as needed. The AI routine 235 may use AI technologies (as described above), for example, Natural Language Processing/Understanding (e.g., for some of the more creative sectors), Fuzzy Logic (e.g., to make basic assumptions), Latent Semantic Analysis (LSA) (e.g., in some sectors), Expert Systems (e.g., in some of the sectors) and/or other technologies. AI routine 235 may, for example, be used to measure against a model, against other entries and look for extreme examples which could determine that a child a natural acumen for a sector.

Once the AIA is completed by the assessment routine 230, an output is generated and provided to the AIA results/feedback routine 250. The output may be generated using, for example, Natural Language Generation (NLG), an expert system, or other technologies. The output may contain information indicating, for example, how much the child enjoyed the game (e.g., based on input from the child and/or parent), how much the child learned (e.g., calculated automatically, and/or based on input from the child and/or parent) and whether the child has any natural acumen or talent in the sector (e.g., as determined by the AIA system). The output or results may include other recommendations such as joining clubs (e.g., after the assessment is completed) associated with a particular sector, performing other activities relating to the sector, contacting an expert in a particular sector, viewing recommended programs, and/or running additional assessments.

A parent or individual supervising the assessment may access the output using the parent interface routine 245. The parent interface routine 245 may be password protected so that unauthorized individuals or children do not have access to the AIA output or results. The parent may provide feedback indicating observations or provide other input relating to the assessment process back to the AIA system. This feedback may be related to the child's performance or reaction to a particular sector assessment. This feedback information from a parent may be used by the assessment routine 230 and/or the game routine 220, for example, to modify or customize future assessments for that particular child.

Figure 3:
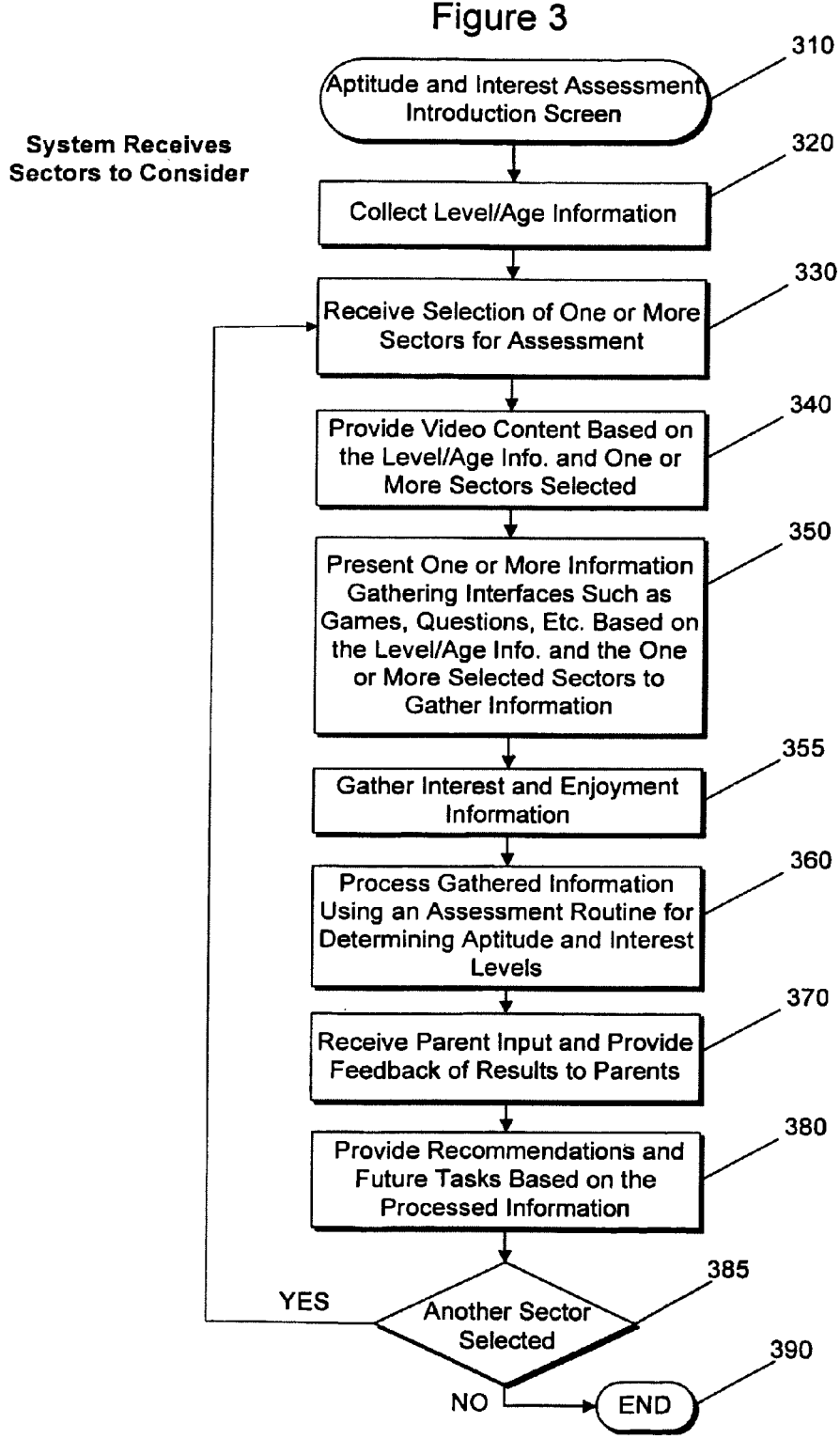
FIG. 3 is a flowchart illustrating a method for assessing aptitude and interest for one or more sectors, in accordance with an embodiment.

FIG. 3 is a flowchart illustrating a method for assessing aptitude and interest for one or more sectors, in accordance with an embodiment. Upon logging onto the AIA interface 130, hosted by the AIA server 140, an AIA introduction screen is presented (310). The client device 120 with the AIA software and content 110 installed may be used to access the AIA interface 130. The interface 130 collects game level information and/or the age of the child (or other individual) for who the assessment is desired (320). The game level information represents the level of the game to be played by the child. The game level may be selected automatically based on the age of the child but may be changed. A list of sectors is presented for selection. The list of sectors may include over 200 occupations, professions, talent areas, fields, and/or areas that can be selected for assessment to determine if the child has a particular acumen or talent for a particular sector. The interface 130 receives the selection of one or more sectors for assessment (330). The various information can be entered by the child or by the parent if the child is young. Once the game level, age and/or sector selections are received, a video may be presented for viewing on the client device 120 (340). The video will be related to the chosen sector (e.g., "a day in the life") and will be at the age level that can be understood by the child. The video may provide information about the chosen sector such as what an individual in that sector does or is required to know, for example. One or more videos can be presented for viewing, if desired.

Once the video is viewed, one or more information gathering interfaces are presented on the client device 120 (350). These information gathering interfaces include virtual worlds, games, question/answer sessions, actions, and/or inputs (e.g., clicks, selections, key board inputs, joystick inputs, or any other types of inputs). The child plays the game and answers the presented questions. Once the game and question/answer session is completed, interest and enjoyment information is requested from the child and gathered by the AIA interface 130 (355). Using a sliding scale, the child can indicate how much they really like or did not like playing the game. The child may also be asked to indicate whether the child learned anything from the interaction or assessment (e.g., knowledge gained information). The child may also indicate whether and/or how much the child enjoyed a chosen sector. The enjoyment indicator is preferably a sliding scale.

The results of the virtual world, game and question/answer session, and other parameter information (e.g., time duration to answer a question, complete a game, make a decision, etc.), as described herein, and is processed to determine aptitude and interest levels the child has for a particular sector (360). A parent can privately logon to the AIA interface 130 and review the results or output of the assessment and provide input back to the AIA interface 130 that can be used for future assessments (370). The AIA interface 130 may provide recommendations of one or more sectors the child may have a interest and/or talent for to the parents (380). The AIA interface 130 may recommend future tasks that the child should perform to further develop their interest and talent (380). The AIA interface 130 may recommend that the child should join a club associated with the recommended sector, perform other activities relating to that sector, work with an expert in that sector, view recommended programs, and/or perform additional assessments. The parent or child can choose another sector (385) and the process can be repeated as shown in FIG. 3. A sliding scale may be used to enable the player to input interest level information (e.g., did the player like the game or session) for a particular game or interactive session.

Figure 4:
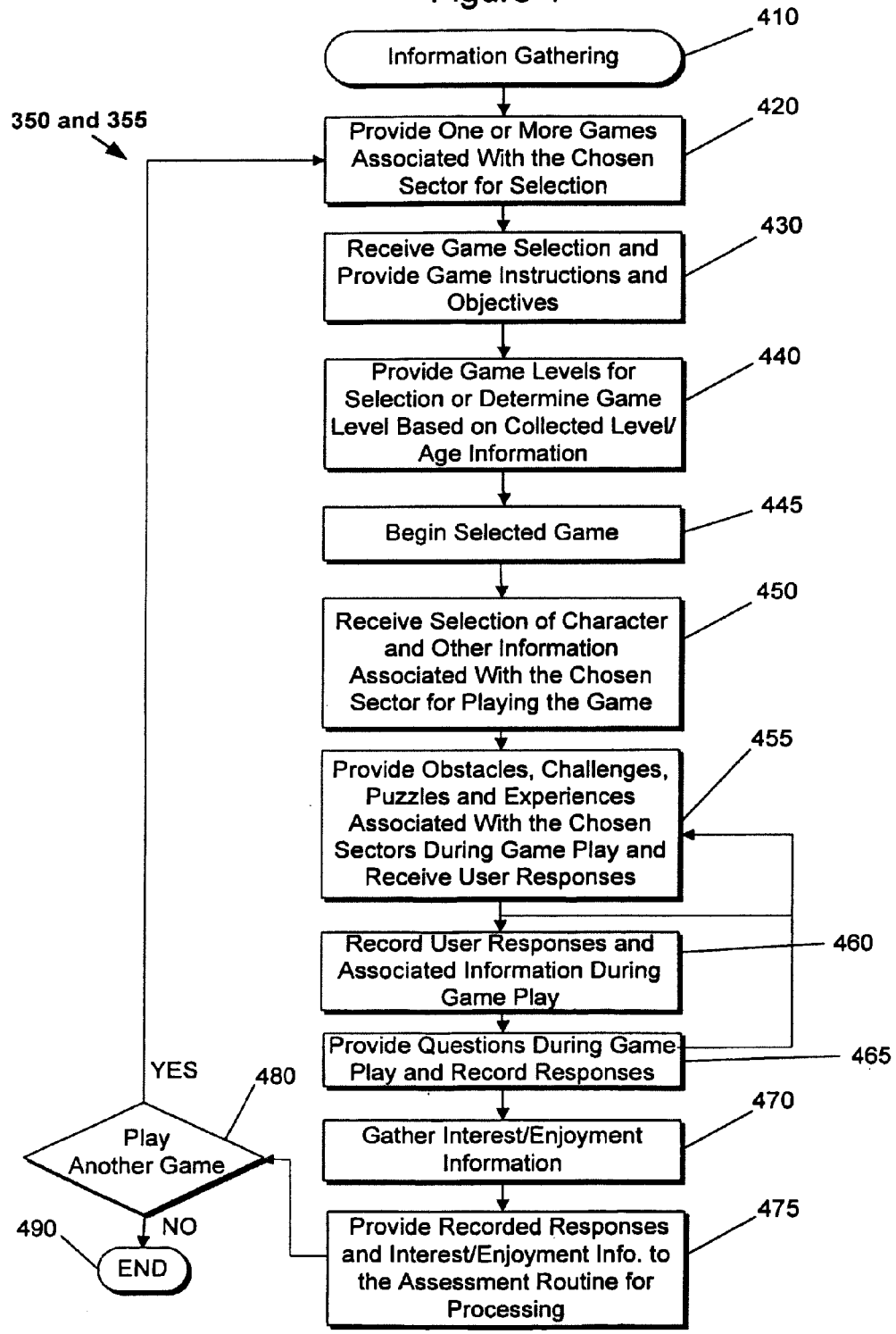
FIG. 4 is a flowchart providing an example of informational gathering performed by the AIA system.

FIG. 4 is a flowchart providing an example of informational gathering (410) performed by the AIA system. The process shown in FIG. 4 details steps 350 and 355, shown in FIG. 3. The AIA interface 130 provides one or more games (including virtual worlds) associated with the chosen sector for selection, during the information gathering (410 and 420). The interface 130 receives information identifying the selected game and provides game instructions and objectives to the client device 120 (430). The interface 130 may provide game levels for selection or may determine level of the game that should be played by the child based on previously collected level and age Information (440). Also, the provided games or experience may be stage one and/or stage two games, as described below. The interface 130 may be a website or may be an interface provided by a stand alone personal computer, CD, DVD, device or game (e.g., a gaming station or a portable game).

Once the game and/or game level have been selected, the selected game can be played by the child (445). Initially, the player selects character and other information associated with the selected and sector. For example, the player can be themselves or a fictional character (or an animal) in the game. In virtual worlds, an avatar may be used. The player can choose a character to be the protagonist in the game or be the protagonist themselves. The character or the player may be associated with the sector chosen for the AIA. The goal of each of the various games that can be played may be different for each game. For example, the game can be an adventure game to meet a goal, complete the game, win money, be king, accumulate points, get meals, etc. The objective of the game may be to go as far as the child can go as a character in the game relying on their talent, skills, intelligence, acumen, for the sector. The player tries to get the most points, money, etc. As the child plays the game, the child is learning about the sector (e.g., profession, sport, etc.). The child can meet people, play in the first person, encounter and overcome obstacles, gain victories, make decisions, laugh and enjoy the game. The games may provide continual pep-talks to the child to keep the child's interest and/or encourage the child. The games may be termed as "B1" (e.g., be the "one" or be the character) and play the game as the character. The games may include humor (e.g., cartoon characters or Three Stooges video) to keep the child's interest and make the game enjoyable. The character may make mistakes ("Uh ohs") and be able to learn from those mistakes. While, the game is played, the child's actions, responses, etc. are recorded and analyzed for AIA purposes, as described herein. There may be over 200 games or virtual world activities (e.g., one for each sector) that can be provided by the AIA system.

The interface 130 receives the character, avatar and other information from the player (450) and processes the information. As the game progresses, the player is faced with, for example, various obstacles, challenges, puzzles and experiences associated with the chosen sectors. As the player progresses through the various obstacles, challenges, puzzles and experiences, the player's responses are received and recorded (455 and 460). The players responses may be used to in real time to provide additional obstacles, challenges, etc. that are used for assessment purposes. As the game continues, associated information and parameters are measured and recorded (460). The other information and parameters may include the duration of a game, the amount of time it takes the player to complete a particular obstacle, challenge, puzzle or objective presented during the game and other information that may be used to determine aptitude or interest associated with a particular sector. In addition, the player is presented with questions during the game and the answers are also recorded (465). Once the game is complete, the interest or enjoyment information is gathered (470) automatically or manually (e.g., input by child or parent). The various responses, measured parameters, interest or enjoyment information, knowledge gained information, and/or other information is provided to the assessment server 140 and used to determine the assessment output (475). If desired, the parent or child can choose to have an additional interactive session such as play another game (480) and the process can be repeated as shown in FIG. 4.

The games may be divided in to one or more stages for player interaction and system assessment. For example, stage one may be a singular experience provided as the player plays the games, and the system assesses aptitude. At the end of stage one, the player may be given suggestions of one or more sectors. Optionally or additionally, in stage two, the player may interact and live out fantasies, especially as they relate to a particular profession. For example, the game may be a game (e.g., an on-line game) providing a virtual world to the child in which the child may face scenarios, obstacles, activities or the like that a person may face in a particular profession. In stage two, for example, a player may play a massively multiplayer online game (MMOG) with other players relating to a profession or talent area.

In an embodiment, the player may accumulate assets and currency, and explore a virtual world. The games may relate to a profession chosen by the player or the profession may be decided based on a questionnaire, a video, a game previously played, determined by the AIA system and/or determined in the virtual world as the player interacts and performs tasks and faces challenges. Stage two may be provided in addition to and/or to confirm the sector identified in stage one.

In some cases, obstacles or challenges faced by the player may be exactly the same as a professional may face during the course of a day, week, month, etc. For example, if the profession chosen or presented is a "doctor," the game may provide an entire world of medicine, for example, for the player to explore. The game may involve a variety of tasks, to some extent or another, such as taking the MCATs (medical college admission tests), going to medical school, being a resident, and/or interfacing with patients, nurses, other doctors, etc. The game may provide an entire virtual word for the player to explore the particular career, profession, or talent area. The game may last hours or days, and the player can choose to continue play and face new obstacles (e.g., a new day or a new challenge) or repeat portions of the game (e.g., the previous day or previous obstacle) to improve performance. The AIA system may assess the players performance in the virtual world game and provide assessment of natural talent in each sector.

In an embodiment, the obstacles or challenges provided in the virtual world may be modified so that they resemble obstacles that a professional may face but the challenges are more appropriate for the age of the player. The obstacle or challenge may be used to gauge (e.g., based on AI systems, formulas, studies, research, expert opinion, and/or a combination of such techniques) how the player may perform in a particular field. The single or multi-stage virtual game or a series of games may be provided on a computer, interactive gaming system, or the like. The computer system may be stand-alone (e.g., a CD, DVD, or downloadable) or may be on-line or a combination of the two. The games could include multi-players so that interaction between other players can be measured, and used to determine the assessment, if desired.

A sector may be assigned a hierarchy of attributes. The attributes may be natural attributes, associated with the profession, rather than taught. Each sector may be assigned at least one attribute that is a "must have" or most important attribute for that sector. The important attribute is defined as a quality or characteristic that a person in that sector must have. For example, a important attribute for an engineer is analytical skills. A sector may have more than one attribute that is considered important for that sector. The sector may have other attributes that are less important for that sector, but nonetheless indicate a quality for a person in that sector. The cross-references attributes and sectors may be stored in an attribute database.

In an embodiment, a player may play a game, for example, to determine the player or user attribute(s). The user attribute may be compared to the important attributes stored in the attribute/sector database. Once a match for the user attribute is found with respect to a important attribute for a particular sector from the database, the corresponding sector or sectors for the matched important attribute may be retrieved from the database. The retrieved sector may represent a sector for which the user may have interest or aptitude.

In an embodiment, a stage two interactive sessions (e.g., games) may provide a virtual world for the player to play and interact. As the player plays the one or more games associated with that sector, the player's performance is analyzed and/or recorded. In this manner, the system can confirm or verify the player high rating for a particular attribute. A routine in the system, such as the assessment routine, may monitor the player's performance to determine or calculate a verified attribute for the player. The verified attribute may be compared with the user attribute to determine or confirm whether the player would actually be successful in the retrieved sector.

In the various interactive sessions, the player may be presented with a plurality of games, obstacles, and/or challenges that are used to determine or verify an attribute. The games may be spread out in the course of several sessions, which may be administered in one day or several different days to make sure that the results are accurate.

The system, individual games and/or assessment tools may include a scoring or ratings interface for the player to choose or enter how they would rate a specific game or task. The scoring or rating interface may include various parameters for the player to enter or select. For example, the player could input how much the player liked a specific game or task, how much they enjoyed playing in that profession and/or whether they might try it in stage two, for example. The scoring interface could also include additional inputs such as how user friendly the game task was or whether there were any specific things that were particularly enjoyable, while others that were not. The scoring or rating interface may include a sliding scale or slider where the child can move a bar to indicate their whether or not they liked a particular game. The scoring or rating interfaces may be designed for kids or adults.

The games and tasks as described herein may be about talent areas and/or professions. In an embodiment, a game or task in a virtual world may permit the player to play games, accumulate possessions, accumulate currency, accumulate points, can create objects and/or a combination of these. The player can create or be provided with a selection of avatars that can be modified and used throughout the assessment. The player can see other avatars and can interact with them as, for example, other players in a profession, and/or "helpers" or mentors. The mentors can also be experts in a particular fields who may assist the players by live interaction, as a computer character or a combination of both.

In a virtual world, the player may interact or live in the virtual world, playing a role or acting out a fantasy, such as in a particular profession. The virtual world may provide a more interactive experience for the player, as the player lives in the virtual world and obtains an identity of a person in a particular sector. In some cases, the player may take a "course" in interaction safety before starting stage two. The system may provide assessments in both stage one and stage two, as the player plays the games and/or interacts in a profession. The assessment results in the various stages may be measured and output separately or collectively.

In an embodiment, the player is able to create content for the games or interactive interfaces. Tools are provided so that the players can create their own content, such as create buildings (like Legos and sandcastles), build a new business, create a new business kit and/or create a new business using a business kit. The players can be guided by experienced or older players (e.g., older kids or experts) mentors for younger kids or inexperienced players to help them use the tools, play games and/or complete tasks.

As a player plays a game or completes a task, they can accumulate currency or points in the various stages (e.g., stages one and two). The player may get the currency for visiting a game, for seeing a video, and/or for playing a game to completion. This currency may represent a reward for the player's accomplishments, that may be redeemed from other players, from sponsors, etc.

The various games or interactive sessions may last for one game, days, weeks or months. A player may register for a make believe adventure and can create his/her avatar, for example. As the player plays the game, the player can build their home or temporary home, explore their environment (e.g., island, city, town), visit places (e.g., restaurant, movies), build possessions, acquire possessions, the player can create content that may become part of their environment and/or the child can create the history for that environment that can be transferred to later game play, stages or other games. While a player is in a game, the player may be transported into another game for a glimpse of future game play, to maintain or arouse interest.

In a virtual world, the player may build a home, open a business, go to a school, practice a profession, accumulate possessions and/or currency, play games (e.g., online games, multi-player online games, massively multiplayer online games (MMOGs), corporate games), interact with the environment, interact with characters, interact with other players, and/or act as an avatar in a sector. In an embodiment, the player may build a dream school which represent the manner the child may want to learn. For example, no boundaries will be set in the school, the school will be fun, personalized and/or offer a wide variety of subjects. This stage may include a stock market for kids, a television network, and/or include games that are collaborative or involve friends.

As described herein, the various games and interaction sessions, are designed to monitor the performance (e.g., action and/or reaction) of the player in the game. The AIA system may use the performance data gathered to assess the player's interest or acumen towards a particular talent area or profession. As used herein, a player can be a child, adolescent or an adult. Although the term "games" is used herein, this term also refers to tools that provide interaction to the player including virtual world tools and are used to gauge performance and/or determine interest or acumen towards a particular talent area or profession. The interaction tools should be enjoyable for the player to maintain interest. On the backend, as described herein, the games may include software, artificial intelligence or similar technologies that process the information gathered from the interaction by the player to calculate or provide feedback. The feedback may include an assessment indicating a particular sector for the player to consider and/or the feedback may include a recommendation of further steps the player may consider (e.g., play another game, consult an expert, watch a video, join a club).

Figure 5:
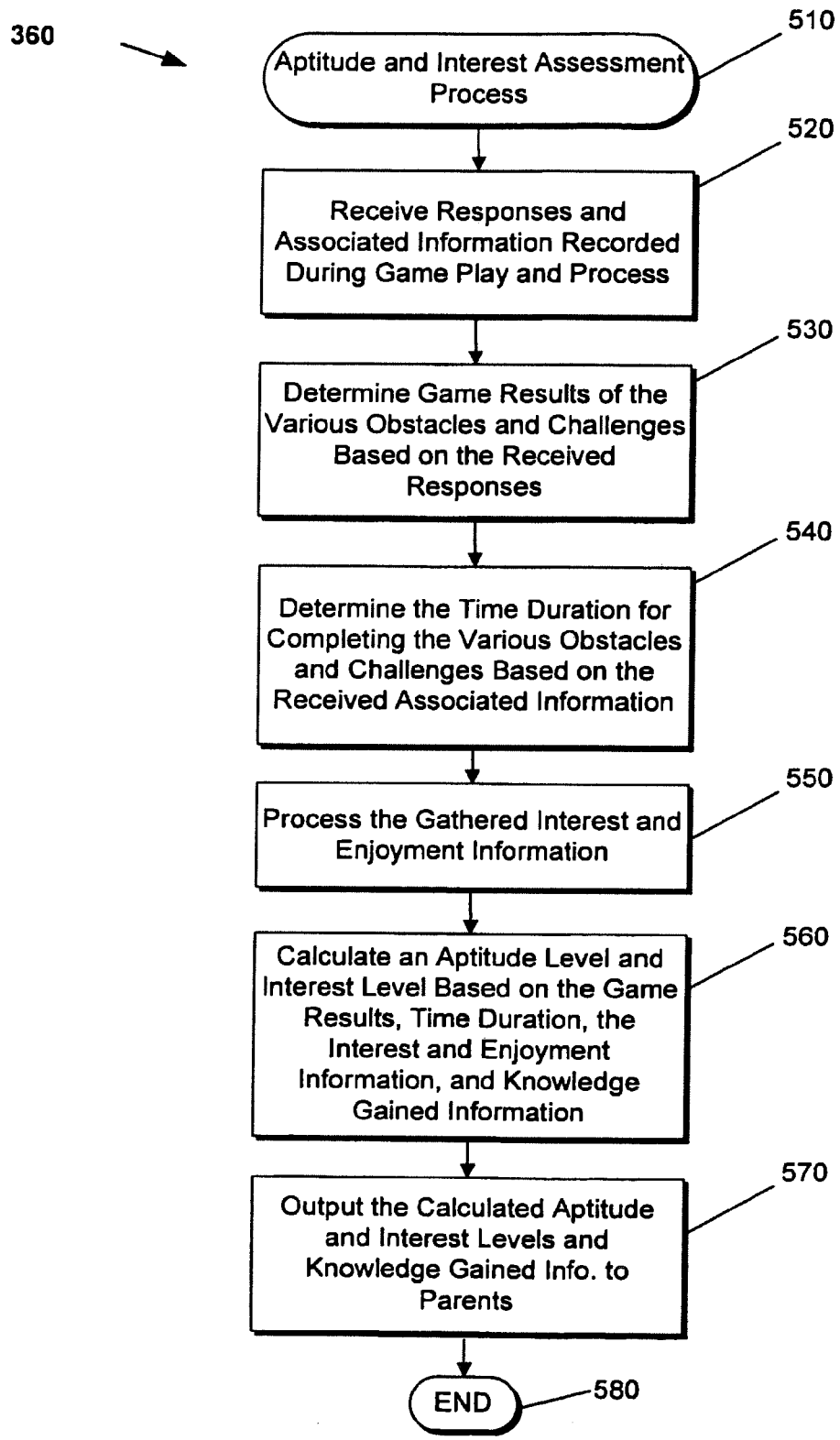
FIG. 5 is a flowchart providing an example of a process that may be used by the AIA interface to determine AIA, in accordance with an embodiment.

FIG. 5 is a flowchart providing an example of a process that may be used by the AIA interface 130 client computer or other device to determine AIA (510), in accordance with an embodiment. This process may use artificial intelligence (AI) to determine the assessment, as described herein. The AIA process shown in FIG. 5 details an example of step 360, shown in FIG. 3. This process may also be implemented in stage one and/or stage two interaction. The AIA interface 130 receives responses and associated information recorded during game play and processes this information (520). As part of the processing of the received responses and associated information, the game results are analyzed to determine results of the various obstacles and challenges (530). A determination is made as to which obstacles, challenges, etc. the player succeeded in completing and which ones the player did not. The various obstacles and challenges may be weighted differently and a sub-total weight may be calculated adding the weights for all the obstacles and challenges that were completed successfully. A total weight may be established by subtracting from the calculated sub-total a weight for all of the obstacles and challenges presented during the game that were not completed successfully. The total weight may be used to determine the child's AIA for a particular sector.

As the player traverses the various obstacles or challenges or answers the questions, many of the player's inputs or answers may be correct, however one or more inputs or answers may be the "best" or required response. If the best response is provided, the "best" response may be compared and analyzed, and given the higher weighting and may play an important role in the AIA process. Optionally or additionally, the currency or points accumulated by the child during game play (or other kids' experiences playing something created by the child) may be used during the assessment process, for example, to determine the child's attributes.

In another embodiment, a variable or other indicator may be used to uniquely represent each attribute by computer language or code. These attribute variables may be used to determine the user's attribute for the assessment. Comparisons can be made by the computer code using the unique identifier.

In addition, the duration of time spent in completing the game (including virtual world) and in completing the various obstacles and challenges may be determined based on the parameters and associated information received (540). The timing information for particular obstacles and challenges may also be weighted and the weights may be considered when calculating the total time for completing a game and/or an obstacle or a set of obstacles, for example. The gathered interest and enjoyment information may also be processed and used for the AIA (550). The AIA interface 130 may also calculate a level of knowledge that may have been gained by the user during the process of watching the video content, playing the game and answering the various questions (or this information may be provided by the child or parent). Once the various information collected from the player is processed, an aptitude and interest level is calculated based on the game results, time duration, the interest and enjoyment information, and knowledge gained information (560) and an output is generated. The output is provided to the parents for analysis (570). The output may contain information indicating how much the child enjoyed the game, profession and/or talent area, how much the child learned and whether the child has any natural acumen or talent in the sector that was chosen for assessment. As described above, the parent may also be provided with other recommendations (e.g., stage three activities) for the child, such as joining clubs, corporate camps, schools and/or training associated with a particular sector, performing other activities relating to the sector, contacting an expert in that particular sector, viewing recommended programs, and/or running additional assessments.

Figure 6:
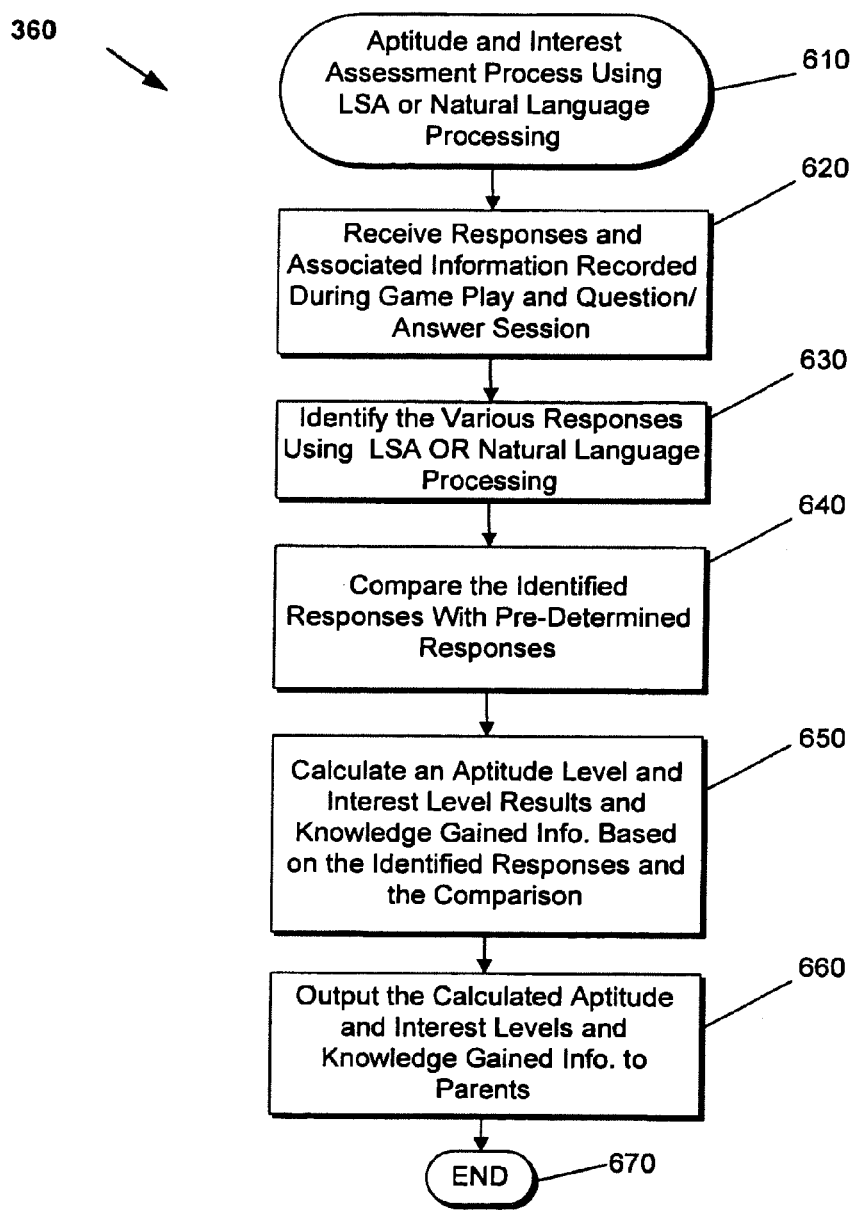
FIG. 6 is a flowchart providing another example of a process that may be used by the AIA interface to determine AIA, in accordance with an embodiment.

FIG. 6 is a flowchart providing another example of a process that may be used by the AIA interface 130 to determine AIA, in accordance with an embodiment. FIG. 6 illustrates the aptitude and interest assessment process also using artificial intelligence technology such as Latent Semantic Analysis (LSA) or Natural Language Processing/Understanding (610). After the player completes the game, the AIA interface 130 receive the responses and associated information recorded during game play, question/answer session, interest and enjoyment information and knowledge gained information (620). In this example, Artificial Intelligence (AI) technologies such as LSA or Natural Language Processing/Understanding may be used to analyze certain input provided by the player. Other AI technologies (as described above) may be used in the AIA processing. AI technology can be used to measure against a model, against other entries and look for extreme examples which could determine that a child a natural acumen for a sector. For example, using AI, typed inputs by the child or parent, on behalf of the child, may be identified and recognized (630). The weighting and "best" answer process (described above) may be used for analysis and assessment purposes. The recognized inputs may be compared to predetermined answers that are system has previously categorized as, for example, extraordinary, best, smart, average or unintelligible answers (640). Thus, the AI system can recognize extraordinary answers to determine whether the child has a natural aptitude or acumen for a particular sector. The AI system can also learn based on the responses recognized and can provide improved analysis with time. The AIA system using the artificial intelligence technology may provide an improved assessment. The system calculates the AIA results and outputs the results to parents (650 and 660).

As the assessment results are processed by the AIA system, as described herein, various skill sets (e.g., judgment, sharpness, quick thinking, etc.) may be identified and scored for the child. One or more skill sets may map to different sectors or talent areas. For example, there may be a "cross pollination" of skill sets among one or more sectors. These skill sets may be used for the AIA to determine acumen, talent or interest for a particular sector or sectors.

Figure 7:
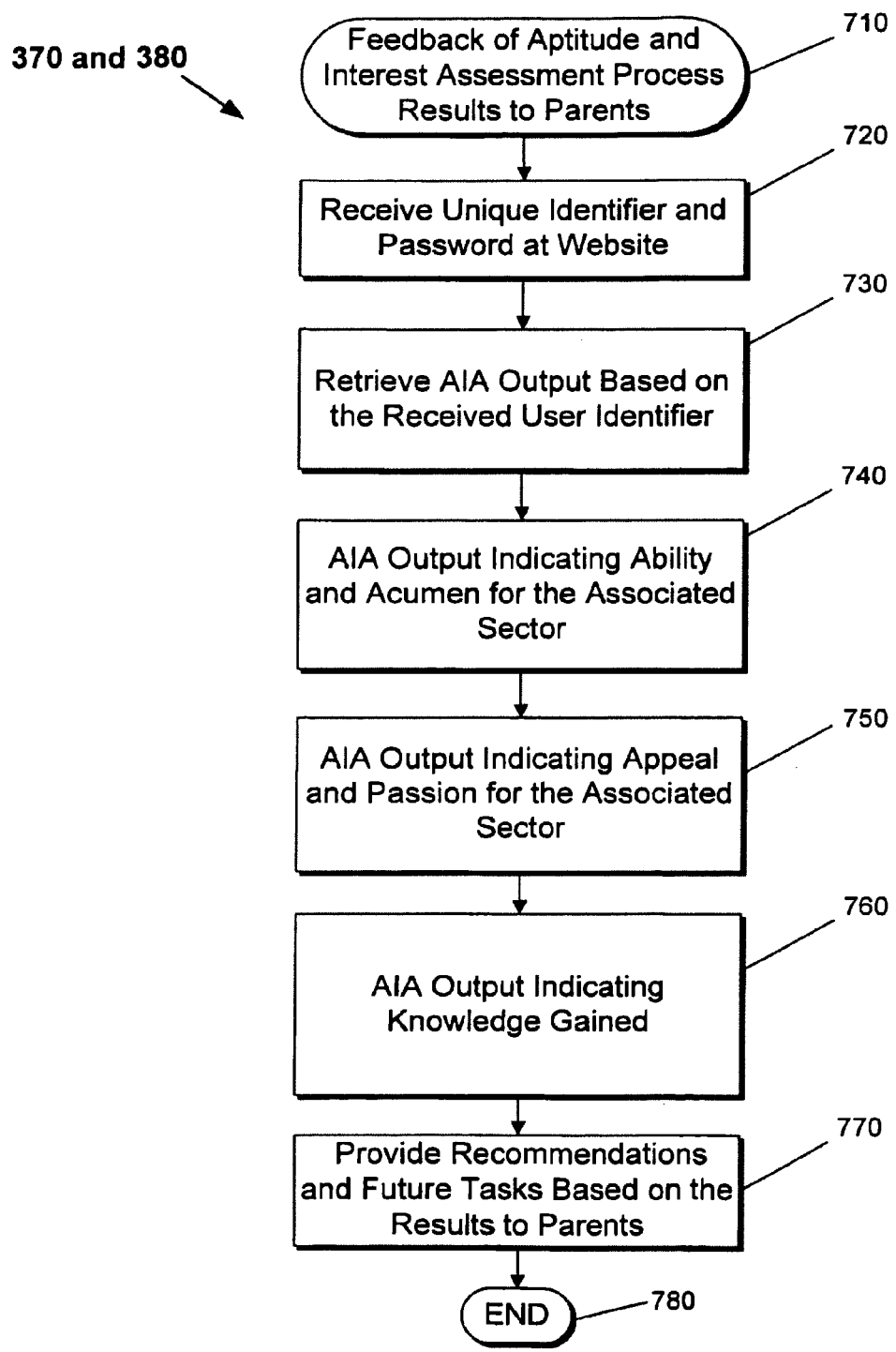
FIG. 7 is a flowchart illustrating an AIA feedback process, in accordance with an embodiment.

FIG. 7 is a flowchart illustrating an AIA feedback process (710). The process illustrated may be used to provide results of the AIA process to parents or other individual supervising or overseeing an AIA. As shown, a supervisor, such as a parent, can log into the MA interface using a unique identifier and password (720). This section may be isolated from the section the child has access to. Once the unique identifier and password are authenticated, the system retrieves the AIA output based on the received unique identifier (730) and provides it to the parent. The AIA interface 130 outputs the results for the sector that was selected for assessment. The AIA output may indicate acumen, ability, interest and/or talent for the associated sector (740). The AIA output may also indicating appeal and passion for the associated sector (750). The AIA output may also indicate whether the child gained any knowledge (760). As described above, the output may contain information indicating, for example, how much the child enjoyed the game, how much the child learned and whether the child has any natural acumen or talent in the sector. The output may include other recommendations (e.g., stage three activities) such as joining clubs associated with a particular sector, performing other activities relating to the sector, contacting an expert in a particular, viewing recommended programs, and/or running additional assessments (770).

Figure 8:
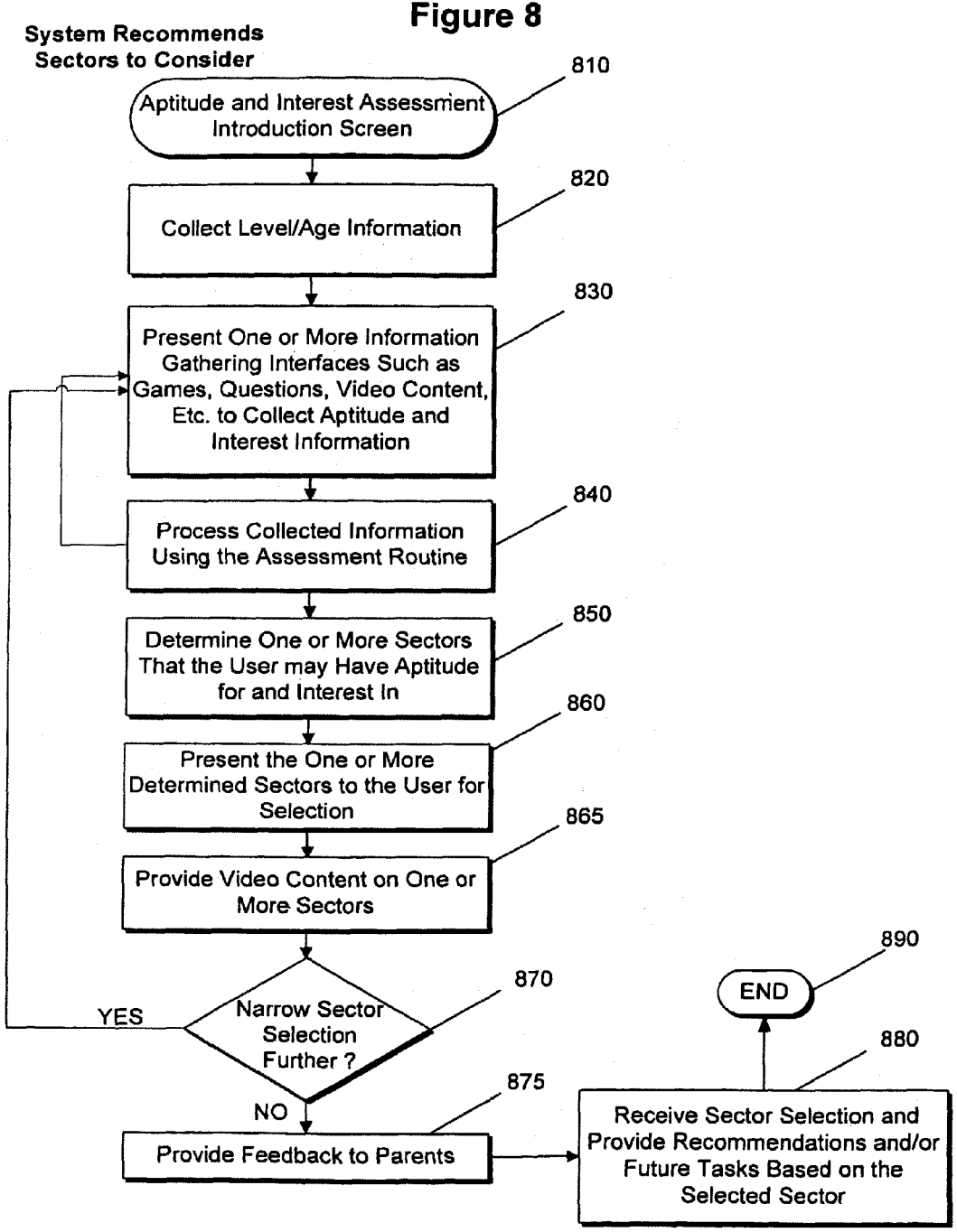
FIG. 8 is a flowchart illustrating a method for recommending one or more sectors for a parent or child to consider, in accordance with an embodiment.

FIG. 8 is a flowchart illustrating a method for recommending one or more sectors for a parent or child to consider, in accordance with an embodiment. The AIA interface 130 presents an introduction screen (810). The AIA interface 130 collects level and age information (820). One or more information gathering interfaces such as virtual world, games, questions, video content, etc. is presented on the client device 120 to collect aptitude and interest information (830). The collected information is processed using the assessment routine 230, for example (840). Based on the processed information (840), additional information gathering interfaces may be provided. The AIA interface 130 may determine one or more sectors the child may have aptitude for and interest in (850). The one or more determined sectors is presented to the user for selection (860). Based on the selection, video content relating to the selected sector (or sectors) may be presented on the client device 120 (865). The sector selection may be narrowed further, if desired (870). If further narrowing is not required, the determined sectors that the child may have acumen for are presented to the parent (875). A sector may be selected and recommendations and future tasks based on the selected sector are provided to the parent (880).

Figure 9:
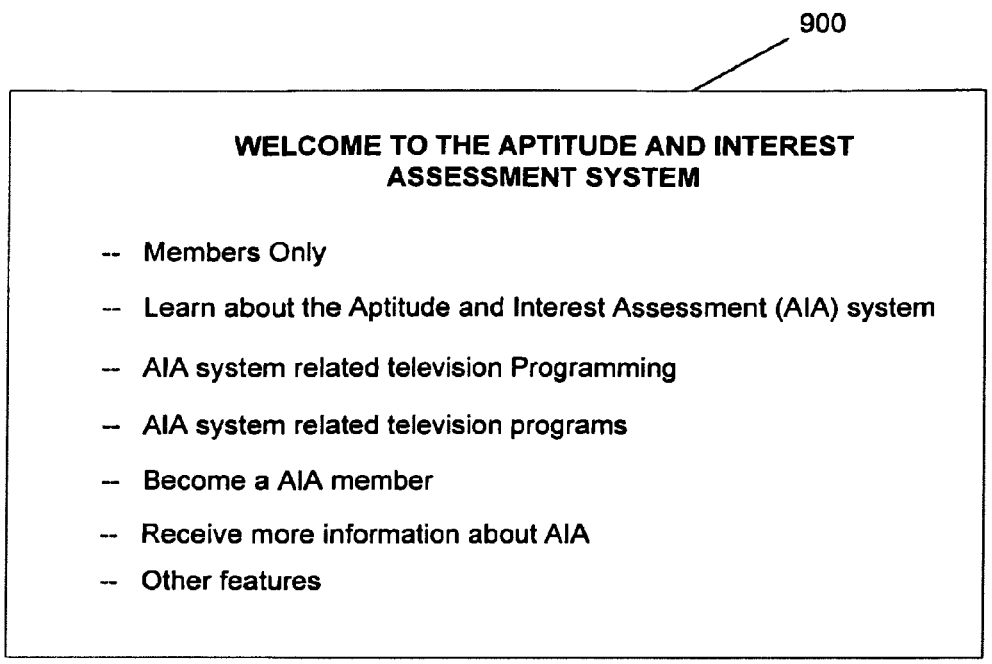
FIG. 9 shows an example of an AIA interface page that may be accessible by AIA system members and non-members.
Figure 10:
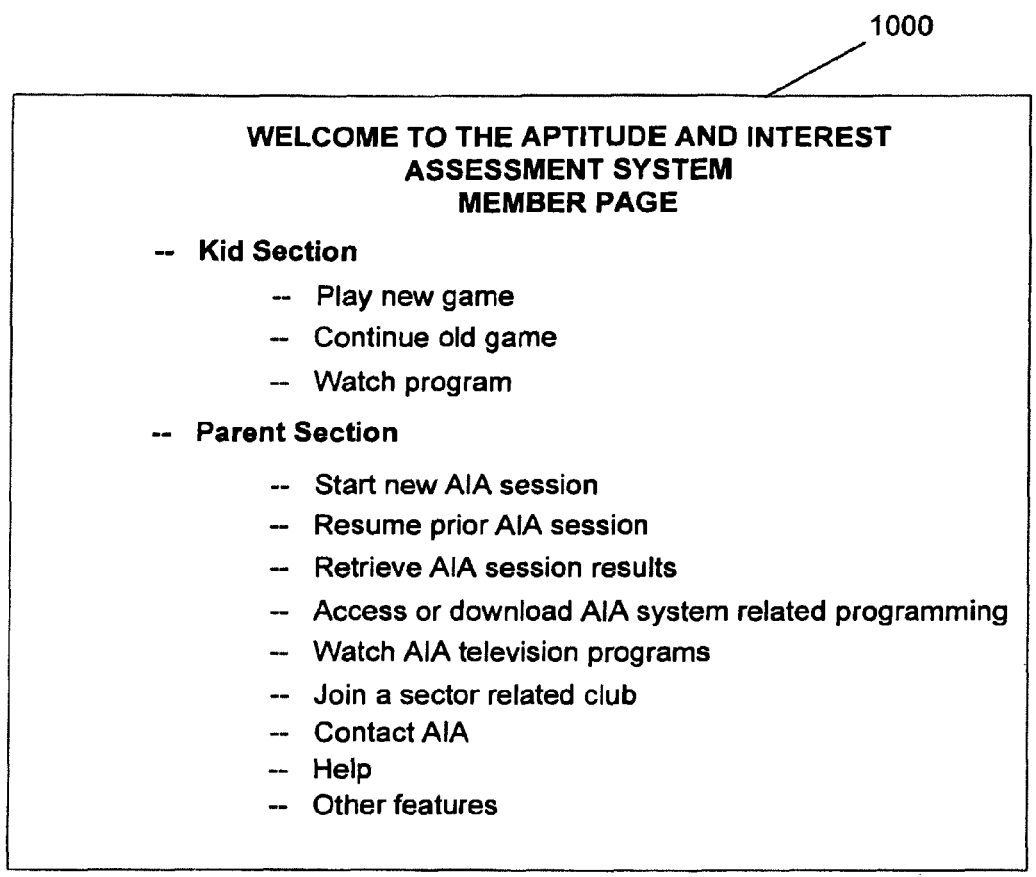
FIG. 10 shows an example of a members only AIA interface page.

FIGS. 9 and 10 examples of web pages that may be presented by AIA interface 130. FIG. 9 shows an example of the AIA home page 900 that may be accessible by anyone (AIA system members and non-members). The home page 900 provides links to "members only" pages and also provides additional information relating to the AIA system. Non-members can receive more information and also become members of the AIA system.

FIG. 10 shows an example of an members only AIA page 1000. Only AIA members with the appropriate subscription can access this page. This page 1000 provides a "Kids Section" and a "Parent Section." If a child is of an appropriate age, the child can run a AIA session using page 1000 without assistance. If a child is too young, a parent or supervisor can run an AIA for the child using the parent section. The parent section may include additional information and links, as shown. These links include a "Retrieve AIA session results" link. This link provides access to the AIA output and results and may require a unique identifier and password for access. Of course, the AIA web pages 900 and 1000 may include additional links. The web pages 900 and 1000 are provided only as examples. In one embodiment, a Parents Virtual World is made available. Parents may interact with other parents and obtain assessment reports or output through the Parents Virtual World.

As described above, in some cases, a "stage three" for parents who want their kids to learn more on a specific talent area may be provided. This may include, a club, a TV show and/or an online TV show, interactive activities, virtual world and even games played against other kids and learning from a role model, quintessential or expert in that sector. The AIA system may provide TV shows with do-alongs, if parent and child choose to play with the show. The child and/or parent may work with national associations in each talent sector and/or a major company in that field and also choose the expert, role model or quintessential in that field. The AIA system may be provided as kit (e.g., that may be purchased, rented, or subscribed to) that includes a DVD or CD-ROM that connects to the AIA websites or interfaces and has videos of a day in the life in each sector or talent area. The kit may also include board games or video/computer games. For example, a parent can order a subscription for a price to receive 15-20 games (relating to different sectors) per period. The AIA system may also be provided as a "granny pack" kit of two games that are sold separately and cover games not in the subscriptions—yet connect online as does the others. Parents may be guided on how to do their own assessments and observations.

As described above, the games measure the individual experience in a game but also the results from similar games and/or skill sets. If there are good results from those similar skill sets this is also important output for the parent and for the assessment. The AIA may use "expert systems" in each vertical to download from specialized expert in that area so that questions/answers/assumptions can be made. Also, other data may be gathered from experts and used for comparison on the performance of a user. This historical or expert data can be used in the analysis or assessment process to compare an expert's performance with that of a user or to combine with other assessment results.

A partial list of sectors or talent areas include:
Small business—entrepreneur
CEO—Boss—Deal maker
Architecture
Sales person—natural born salesman
Technologist
Chef
Inventor—making things better—improvements
Inventor—seeing things/creating what others don't see
Doctor
Film Maker
music creator
fiction writer—story teller
reporter
detective—solving things Ad creator
TV producer
games or toy developer
space—or the Sea
fashion-designer
computers—CS
politician—debater
archeology
languages
veterinarian
engineer
helping people
robotics—
carpentry—builder
loves foreign countries—cultures
loves money—banker—investments
artist
teacher
athlete or sports related career (baseball player, football player, basketball player, etc).

The above list is only a partial list and any number of professions, fields, areas, talent areas can be included and used in the AIA process described herein.

Figure 11:
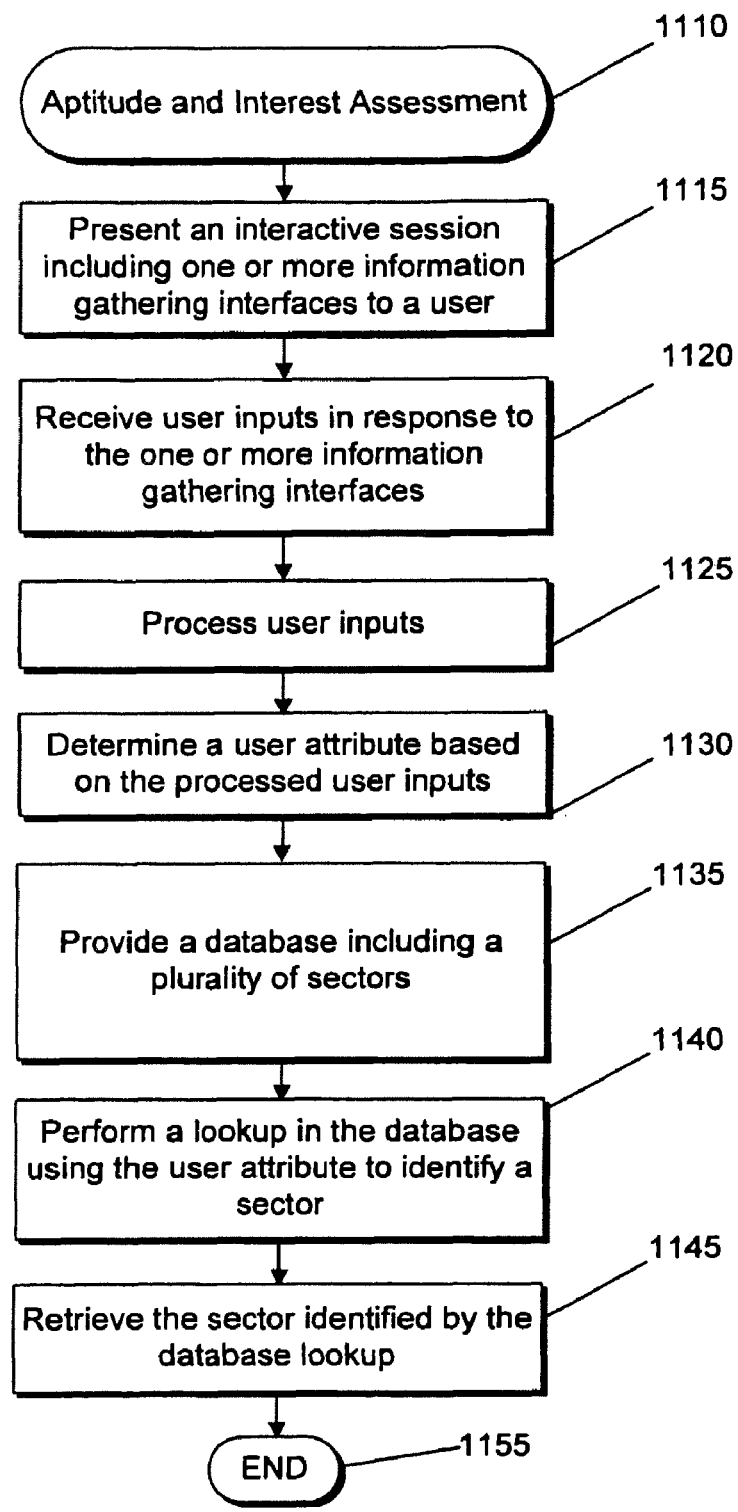
FIG. 11 is a flowchart illustrating a method for retrieving a sector in a aptitude and interest assessment system, in accordance with an embodiment.

FIG. 11 is a flowchart illustrating a method for retrieving a sector in a aptitude and interest assessment system, in accordance with an embodiment. An aptitude and interest assessment session may start with an interactive session presented to a user, as shown in 1115. The interactive session may include one or more information gathering interfaces to solicit information from or about the user. The information gathering interfaces (including virtual world) may be provided via user interface module, which may be any input device or input means or interfaces. The information gathering interfaces may be games, questions and/or other input requests to gather information from the user. User inputs are received in response to the one or more information gathering interfaces, as shown in 1120. The user inputs are processed, as shown in 1125. The user inputs may be processed using an assessment module (e.g., 230).

A user attribute is determined based on the processed user inputs, as shown in 1130. The determined user attribute indicates the user's aptitude or interest for a particular sector. The user attribute may indicate the strength of the user in that attribute. In one example, questions or situations presented in the various information gathering interfaces (e.g., actions during game play, questions during game play, question answer sessions, expert consultation session, etc.) may be associated with one or more attributes. For example, if a user is performing a task or mission in a game and a particularly interesting event (e.g., a news worthy event) occurs in the game, the user may be provided with the option to continue previous task or to pursue new event. If the user decides to pursue the interesting event, that decision indicates that the user has an investigative attribute (e.g., a nose for news). This investigative attribute would be an attribute that is important for a reporter or a detective.

In an embodiment, each question or situation may be tied to one or more attributes. In one embodiment, a single attribute may be associated with each sector. The single attribute is compared with the user attribute to determine if the user has an interest or aptitude for the corresponding sector.

Optionally or additionally, one or more attributes may be configured in a hierarchy of attributes, ranging from the most important attribute (e.g., having the highest importance level of 1), to the second most important attribute (e.g., having the importance level of 2), to the third most important attribute (e.g., having the importance level of 3), etc. The hierarchy of attributes may include any number of attributes. In an example, the hierarchy may include 5 attributes, ranging from an importance level 1 (e.g., most important) to an importance level of 5 (e.g., least important). The hierarchy of attributes may be weighted. The highest weight may be assigned to the most important attribute and the lowest to the least important attributes.

Optionally or additionally, a user's response time (e.g., the time the user takes to react to a question, to make a decision, to respond to a situation) may be measured. The measured response time may be used as part of the determination or calculation of the user's attribute. In one example, if the user's response time is greater than a response time threshold, then the system may determine that the user does not have the attribute associated with the question, answer or situation presented. If the response time is less than the threshold, then it may be determined that the user does have the attribute associated with the question, answer or situation presented.

In one embodiment, attributes are used for aptitude and interest assessment. Attributes are unique and specific traits that relate to particular sector. A unique or special language may be used to define attributes for each sector. For example, an attribute for a pilot may be "keeps calm, doesn't lose control." As another example, the attribute for TV reporter may be having a "nose for news." These unique and specific attributes may be specifically assigned to the appropriate sector.

In another embodiment, abilities may also be used for aptitude and interest assessment. Abilities may be general traits relating to a particular sector or profession. Attributes, on the other hand may be unique and specific to a sector or profession. The abilities may be used in combination with attributes.

Abilities include, for example, abstract reasoning, analogic reasoning, attention, auditory discrimination, cognitive flexibility, cognitive fluency, common sense, concentration, deductive reasoning, expressive language, eye-hand coordination, fine motor coordination, gross motor coordination, ideational fluency, inductive reasoning, logical reasoning, long-term auditory memory, long-term sequential memory, long-term verbal memory, long-term visual memory, mental manipulation, mental planning, nonverbal concept formation, nonverbal reasoning, numerical reasoning, receptive language, short-term auditory memory, short-term sequential memory, short-term verbal memory, short-term visual memory, sequential processing, simultaneous processing, social judgment, verbal analytic reasoning, verbal concept formation, verbal processing, verbal synthetic reasoning, visual analytic processing, visual discrimination, visual-motor coordination, visual synthetic processing, visual perception, visual perceptual accuracy, visual perceptual reasoning, visual processing speed, visual scanning, visual-spatial organization, visual tracking, and working memory.

The identification of an attribute or hierarchy of attributes, for each sector, may be based on information received from a quintessential (e.g., an expert in the area) in that sector, a major corporations in that sector, a child development expert, a national association, surveys, other research and/or major search firms/experts who know what attributes are most significant or desirable in a particular sector. This information may also be used to determine the hierarchy and/or weights for the attributes. Information on important or desirable attributes for sectors may be gathered, analyzed, identified and determined. The cross-references attributes and sectors may be stored in an attribute database. Checks and balances are applied so that the attributes and/or attribute hierarchy information is based on a census of experts or sources.

In an embodiment, if a user answers a question or reacts in a certain manner, this indicates that the user has a particular attribute required or desirable for a particular sector. However, if the user does not answer the question or react in a certain manner, this indicates that the user does not have that attribute, thus the user would not have an aptitude or interest for that sector.

In an embodiment, it is required that the user have the most important attribute of the sector in order for the sector to be recommended or suggested. In another embodiment, even if the user does not have the most important attribute, the user may have a combination of other attributes in the hierarchy of attributes that indicate that the user may have an aptitude or interest for a particular sector. The user's attribute or attributes can be determined in one interactive session (e.g., in one game or virtual world session) or a series of interactive sessions. The series of interactive sessions may be presented over a period of time, providing an accurate result of the attribute possessed by the user.

In an embodiment, the user's aptitude may be calculated using, for example, the information received from the user as well as information from experts, research, etc. Different techniques may be used to calculate the user's attribute. For example, a normal or average score may be established for one or more attributes associated with a sector. The norm or average can be used as a benchmark. As the user interacts during the information gathering sessions, the user's inputs are used to calculate a score for the user associated with the one or more attributes. If the user's score falls, for example, in the top 10%, 15%, 25%, etc. ranking as compared to the average score for the associated attribute, the user may be credited with that attribute. This scoring information is used determine if the user has the attribute that is required for a particular sector. If a user falls below the average score, the system may determine that he does not have the attribute.

An attribute database including a plurality of sectors is provided, as shown in 1135. The attribute database may be stored anywhere in the system shown in FIGS. 1 and 2. Each of the plurality of sectors in the database may be assigned or include one or more attributes. These attributes could be listed as entries associated with each sector or may be mapped to each sector. The one or more attributes may be the most important attribute or attributes, or may be a hierarchy of attributes associated with the sector. The attributes and/or hierarchy of attributes associated with each sector and, populating the attribute database, may be determined as described above. A database lookup is performed using the user attribute to identify a sector, as shown in 1140. The sector or sectors identified by the database lookup may be retrieved, as shown in 1145.

Any number of techniques may be used to identify and/or retrieve a sector or sectors from the database. In one example, the database may be searched for all sectors having an entry that contains the user's attribute. Sectors that have the user's attribute as the important or most important attribute, in the hierarchy, may be retrieved as sectors that may be relevant to the user. Thus, In one embodiment, matching the most important attribute returns a recommended sector. Optionally or additionally, sectors that have the user's attribute as the top two or top three most important attribute may be retrieved from the database. Other techniques may be used to retrieve a sector or sectors from the database based on the user attribute.

As stated above, the interactive sessions may present one or more interactive gaming sessions to the user. The gaming sessions may provide various challenges or obstacles for the user to overcome. The user's performance in dealing with the various challenges or obstacles may be monitored and the user attribute may be determined or calculated by these responses.

In an embodiment, a sector for which the user may have aptitude or interest is identified during stage one interaction. Once the sector is identified, the user may be presented with stage two interaction. The stage two interaction may be a confirmatory interactive session used to confirm whether the user has the aptitude or interest for the identified sector. The stage two interaction can include additional interactive games and/or interactive sessions. For example, the user may be provided with a virtual world. In the virtual world, the user may interact with other users (e.g., a multi-player game) or play alone. In the virtual world, the user may play out a particular profession, for example, by using an avatar acting out the profession. The avatar may be a character that the user creates or an avatar selected from an available assortment of avatars. The avatar may be used throughout the assessment process (e.g., for multiple games or interactive sessions). The avatar may represent the user and the avatar may inherit the attributes or traits of the user during the assessment process or interactive sessions.

In stage two, the user may face challenges or obstacles, in the virtual world, associated with the identified sector. The performance of the user may be monitored over the course of the game or games in the virtual world to verify that the user has aptitude in or for that sector. More specifically, whether the user possesses one or more of the attributes needed for the particular sector. A verified attribute for the user based on the user interaction in the second stage (e.g., the virtual world in the identified sector) is determined or calculated. A reverse lookup operation is performed in the database using the identified sector to identify an attribute associated with the identified sector. The verified attribute is compared with the attribute identified in the database to confirm that the user has aptitude or interest for the identified sector based on the verified attribute and the identified attribute from the database. If the verified attribute matches the identified attribute, identification of the identified sector is provided to the user. The match confirms that the user has aptitude for the identified sector. If the verified attribute does not match the identified attribute, an indication is provided to the user that the user does not have aptitude for the identified sector.

If the verified attribute does not match the identified attribute, another database lookup may be performed using the verified attribute to identify and/or retrieve a revised sector. Once the revised sector is identified or retrieved, the user may be notified of the revised sector. Also, another second stage interactive session may be presented to the user. This second stage is a virtual world used to confirm whether the user has aptitude or interest for the revised sector.

In an embodiment, a confirmation, whether the user has aptitude for the sector, is accomplished by directly comparing the user attribute with the verified attribute. In this embodiment the user attribute is typically stored in memory from early interactions with the user. If the verified attribute matches the user attribute, identification of the identified sector is provided to the user. This match confirms that the user has aptitude for the identified sector. If the verified attribute does not match the user attribute, another lookup is performed in the attribute database using the verified attribute to identify a revised sector. Further assessments or interaction games may be presented to the user to confirm and/or fine tune the assessment results.

Figure 12:
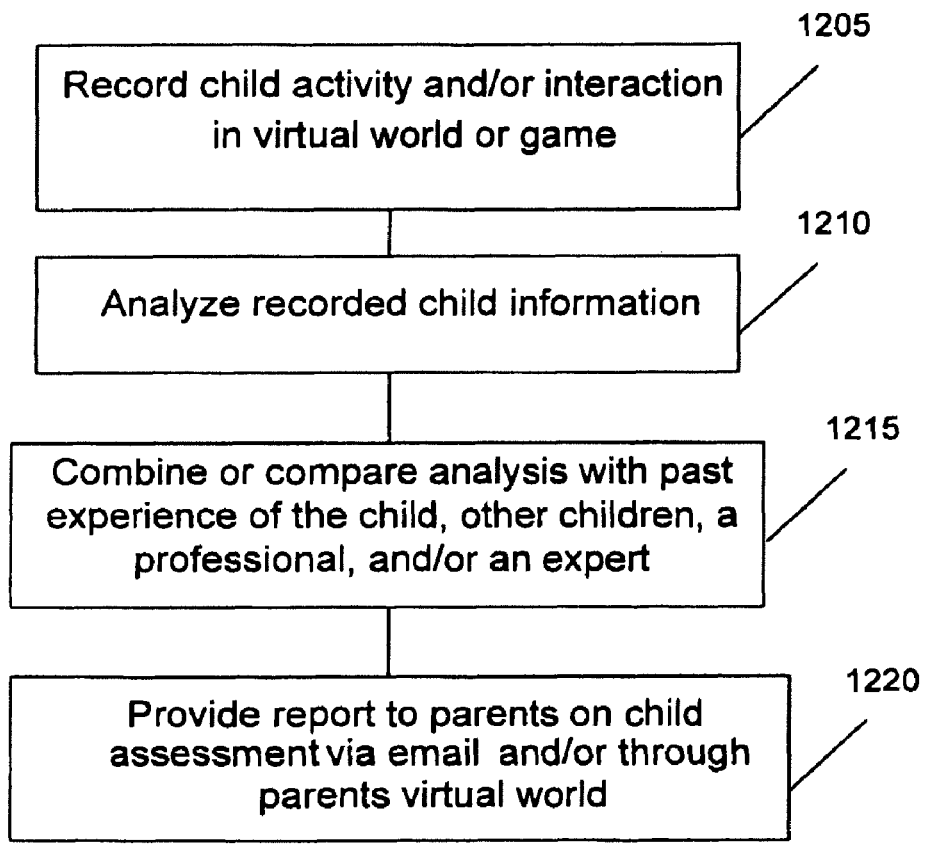
FIG. 12 is a flowchart illustrating a method for assessing aptitude and interest for one or more sectors, in accordance with a virtual world embodiment.
Figure 13:
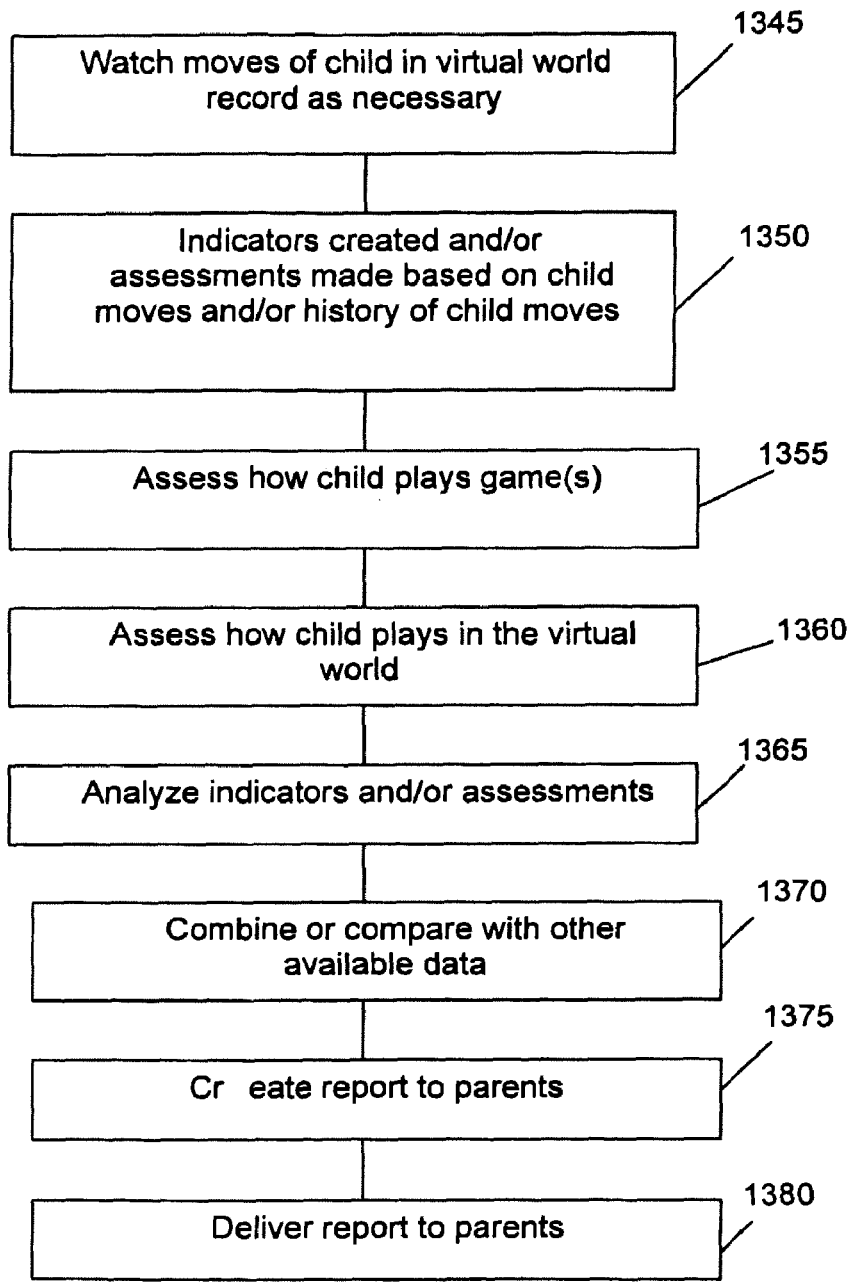
FIG. 13 is a flowchart illustrating a method for assessing aptitude and interest for one or more sectors, in accordance with another virtual world embodiment.
Figure 14:
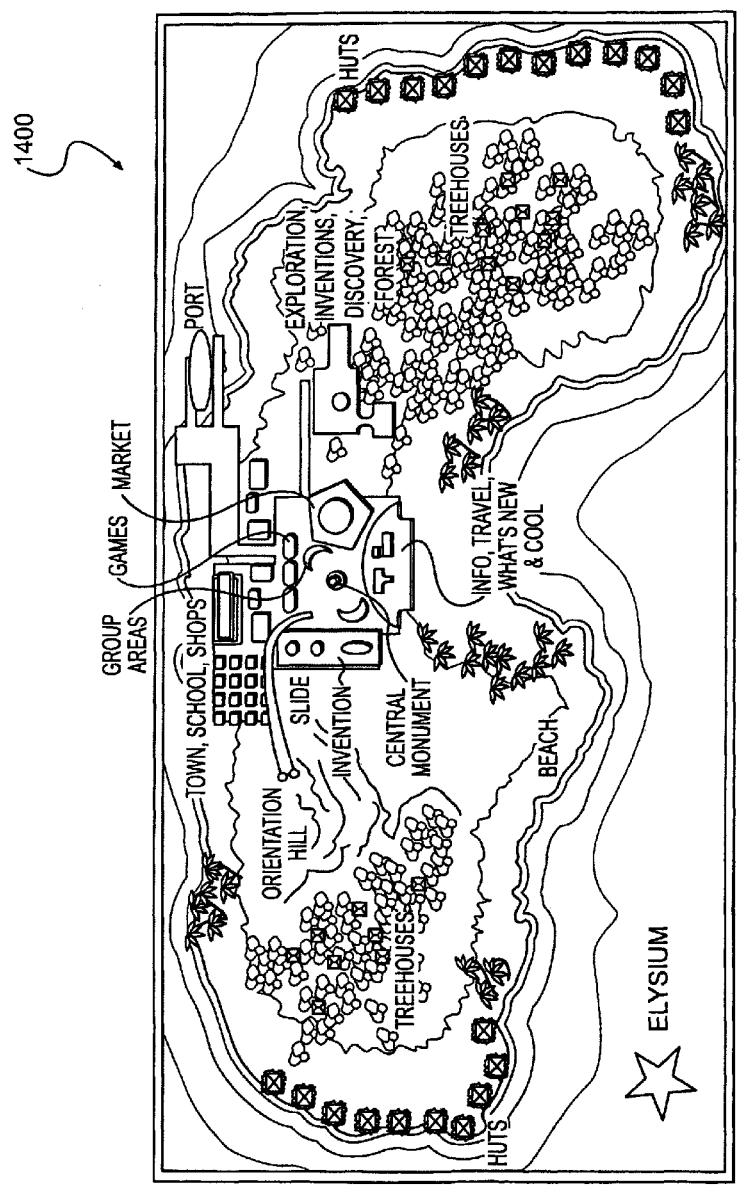
FIG. 14 shows an embodiment of an island in a virtual world.

The games or interaction tools may include a variety of input interfaces or techniques for the player to input information. For example, a player may use a mouse, a keyboard, helmet, gloves or other such interface tools. In an embodiment, the system may include an interface tool that can help younger children express themselves. FIGS. 12, 13 and 14 relate primarily to a virtual world embodiment. With regard to FIG. 12 embodiment is shown in which virtual world activity is recorded, analyzed, combined or compared, and reported. Specifically, user activity and or interaction in the virtual world is recorded and stored in a storage device or memory 1205 The recorded information is then analyzed in a processing step 1210 The analyzed information is then compared or combined with past experiences of the user, other users, a professional and/or an expert 1215 By comparing this information or combining the relevant information with past experience a report can be provided. The report can be provided via electronic means such as electronic mail and/or through a virtual world 1220

In most embodiments the user will be a child or young adult and the virtual world or games would be played by the child or young adult. A parent's virtual world may be created by the system for parents to interact with other parents and for parents to obtain information about the child's virtual world as well as to retain reports on the child's assessment and aptitude. The parent's virtual world becomes a social network in which parents may swap information and stories about their children.

FIG. 13 is another virtual world embodiment. The first step in this embodiment is that the system watches the moves of a child in the virtual world and records those moves as necessary to monitor the child's aptitude and assessment 1345 Indicators are created based on the moves which are recorded in Step 1345 Not all moves in the virtual world and not all the raw data from the moves in the virtual world are needed in order to perform an assessment of aptitude and interest. Also the raw data from the moves in the virtual world are often not in a format that's appropriate or easily used in performing an aptitude and interest assessment. Therefore, in this embodiment the raw data of the moves in the virtual world are converted or saved as indicators by screening out some of the moves and/or by converting or processing the move data if necessary 1350 Alternatively, in an embodiment the assessment can be made based directly on the moves or raw data from the virtual world 1350.

The history of a particular child's prior moves or historical data on other children's moves in the virtual world can be used in performing an assessment 1350 One of the things that can be assessed is how a child plays particular games in the virtual world 1355. Also, the system may assess how a child handles himself or plays in the virtual world such as how well he does at a profession in the virtual world, how well he does at activities, tasks or obstacles in the virtual world 1360. In this manner the child's conduct or performance in the virtual world is monitored to assess his aptitude and interest in particular professions, sectors or areas of life 1360 The indicators recorded and/or assessments observed or recorded in this process are then analyzed in order to create data which may be used for a final comparison and generation of an assessment report 1365. This analysis of indicators and preliminary assessments made for example in steps 1350, 1355 and 1360 may be analyzed, process and assessed as described elsewhere in this specification.

In addition, it will be appreciated that various methods of analysis of the indicators or analysis of the preliminary assessment data may be performed. Some of these analyses may be as simple as determining whether a user in the virtual world has reached a certain goal or a plateau. Other methods include comparing the performance of the user or child with an adult, a professional in the field or sector, or experts in a particular field or sector. Therefore, while analysis of the data may be made to determine user attributes indicating an aptitude or interest of the user in a particular sector, various modifications and variations are possible.

A list of items that may be used as indicators or for assessment include the following:

Is the child a pioneer and/or does child explore new lands?
Does the child like to be first or an improver?
A team leader or a team player?
Like to invent and what types of things invent
Like to create new games
How they do in a certain profession?
How do they feel about currency and/or obtaining things?
Do they "give back" to the world and/or to other kids?
Like to create videos
How expansive is their imagination?

In the embodiment shown in FIG. 13, the analyzed data is compared with other available data to help create an assessment report. Alternatively, the analyzed data may be combined with other information or other data in order for the report reader to have some baseline information or comparison information to reach the report readers conclusion 1370. This available data may be historical data, past experience data, or data from other users, data from professionals, experts, older children, or adults. This available data maybe stored in various locations throughout the system.

In the embodiment of FIG. 13, after the comparison or combination is performed 1370, a report is created 1375 and the report is delivered to the report reader 1380. Various methods of creating a report may be used including methodologies known from database report generators. Reports my be delivered to report readers such as parents by hard copy, by electronic means such as electronic email, text messaging, voice messages and virtual world means. In addition, an entire separate virtual world may be created such as a parent's virtual world in which the parents may access the report and assessment information by entering the parent's virtual world and interacting with the parent's virtual world.

FIG. 14 shows an embodiment of an island in a virtual world in which user would interact in order for an aptitude or interest assessment to be conducted 1400. Some activities that a user may participate on the island include exploration in the virtual world of other lands or islands, creation of inventions in various technology areas, discovery work for example in the areas of nature and science and forestry. A user may participate in the market area of the island by operating a store or shop in a business-like fashion. Games as well as participation in town school activities are available on the island. Users may also gain further information about the virtual world, travel within the virtual world and examine what's new or cool in the virtual world. The island has a port available in the virtual world allowing users to leave and return to the island as well as to perform various sailing or water activities. Tree houses, huts and beaches are available to users for various activities and games. The island 1400 is an example of many islands or locations which may be available in the virtual world for the user to participate in various activities, obstacles, challenged, professions and events.

FIG. 15 illustrates an input interface tool that may be provided in, for example, the AIA system. For example, the interface tool may include a "bag of words" tool that provides words, phrases, icons and/or images the child can choose from to create responses and interact or connect to the AIA system. The interface tool may present a question, as shown in the interface screen 1200. The interface tool may also provide a plurality of categories associated with the question on the interface screen 1220, as shown. Each category from the plurality of categories may include a plurality of entries relating to the question. A combination of the plurality of entries may represent one or more answers to the presented question. For example, as shown in FIG. 15, the interface screen 1200 includes a question "Tell us what type of pet you would like?" Below the questions are presented four categories (e.g., category 1, category 2, category 3 and category 4) containing entries the user can choose from to answer the question presented. The user may chose one entry from each category or multiple entries, if appropriate. The user may not need to chose an entry from each category, as long as the complete answer is provided. The bag of words tool may be provided by, for example, a child/user interface routine or module 210, as shown in FIG. 2.

Figure 16:
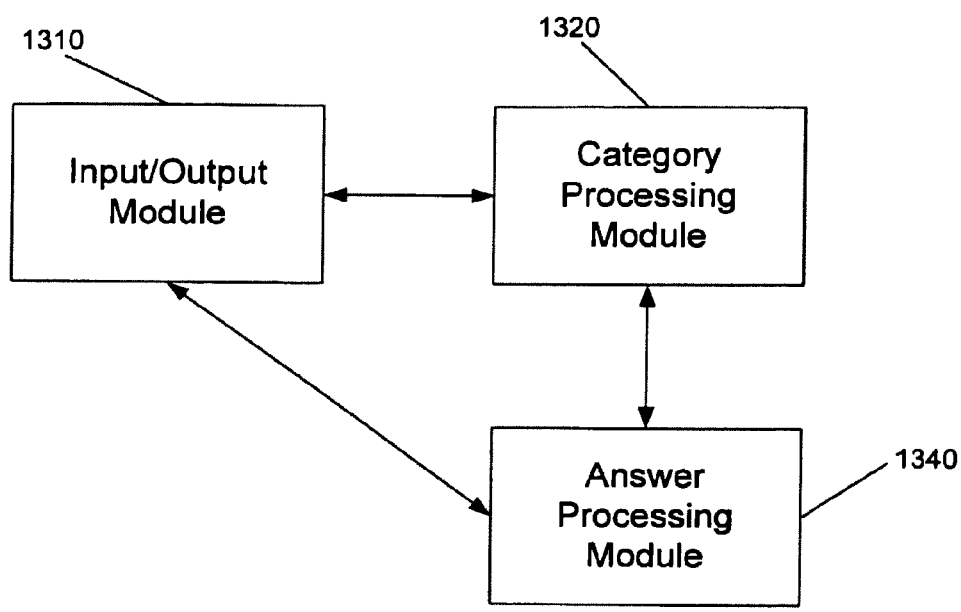
FIG. 16 illustrates a block diagram of a input interface system, in accordance with an embodiment.

FIG. 16 illustrates a block diagram of a input interface system described in FIG. 15, in accordance with an embodiment. The system may include a input/output module 1310, a category processing module 1320, and a answer processing module. The input/output module 1310 presents a question on a user display. The category processing module 1320 provides a plurality of categories on the user display. Each category from the plurality of categories comprises a plurality of entries relating to the question and wherein combinations of the plurality of entries represent answers to the presented question. The answer processing module 1340 receives a user selection of one or more entries from the one or more of the plurality of categories. The user selection represents an answer to the presented question. The input/output module 1310 may also present the selection to a user on a user display for viewing. The selection representing the user's answer to the question.

The input/output module 1310 may include an audio output module to provide an audio output of the selection, questions, answers, categories and/or other information. This can be accomplished with text to audio conversion. The audio output representing the user's answer may require the user to confirm that the answer generated by the interface is correct. This confirmation may occur via the input/output module 1310. In an embodiment, artificial intelligence or other techniques may be used by the category processing module 1320 and/or answer processing module 1340 to generate the categories, the questions, the answers and/or to confirm that the user's selection provides a meaningful answer to the question presented. Multiple screens may be presented to the user to present questions and receive answers from the user.

The categories provided for selection may include entries in the form of words, icons, images, colors, shapes, or the like, as appropriate. The words may include nouns, verbs, adjectives, adverbs, for example, that the child can choose from to respond to the question presented. The user may simply select or click on the desired entry from the appropriate category, or may drag the entry to a location on the screen where the answer is indicated. The bag of words tool may use previous answers to determine which words or phrases should be presented for selection. This tool is particularly helpful for a person that has difficulty reading, typing or spelling.

The various interactive sessions, processes, interfaces and assessments described above may be implemented in the one or more components, modules, software and/or routines described above and shown in FIGS. 2 and 3. Optionally or additionally, other components, modules, software and/or routines may be used to implement the various interactive sessions, processes, interfaces and assessments described above.

Several embodiments of the present invention are specifically illustrated and/or described herein. However, it will be appreciated that modifications and variations of the present invention are covered by the above teachings and within the purview of the appended claims without departing from the spirit and intended scope of the invention.

The invention claimed is:

1. A system for aptitude or interest assessment, the system comprising:
   a user interface module adapted to present an interactive session to a user, wherein the interactive session provides one or more information gathering interfaces to the user, and wherein the user interface module is adapted to receive user inputs in response to the one or more information gathering interfaces;
   an assessment module adapted to process the user inputs received from the one or more information gathering interfaces and is adapted to determine a user attribute based on the processed user inputs, wherein the user attribute indicates an aptitude or interest of the user for a profession;
   a database containing a plurality of sectors, wherein each of the plurality of sectors respectively corresponds to one or more professions, wherein each of the plurality of sectors is assigned one or more sector attributes, wherein each of the one or more sector attributes represents a trait for that sector, and wherein the assessment module is adapted to perform a comparison in the database using the user attribute and the one or more sector attributes to identify a sector from the plurality of sectors and retrieve the sector identified by the database comparison; and
   a report creator that creates a report indicating the retrieved sector.

2. The system of claim 1, wherein the one or more sector attributes comprise a hierarchy of a plurality of sector attributes.

3. The system of claim 2, wherein the hierarchy of the plurality of sector attributes comprises a most important sector attribute, a second most important sector attribute and a third most important sector attribute.

4. The system of claim 1, wherein the assessment module is further adapted to retrieve a predetermined attribute correlated to a user input from the processed user inputs.

5. The system of claim 1, further comprising:
   an information collection module that measures a user response time for receiving a user response to one or more situations presented during the one or more information gathering interfaces, wherein the user response time is used to determine the user attribute.

6. The system of claim 5, wherein the assessment module does not determine the user attribute if the response time measured by the information collection module is greater than a response time threshold.

7. The system of claim 1, wherein the one or more information gathering interfaces presents a situation and the user interface module is adapted to receive responses to the situation presented.

8. The system of claim 1, wherein the assessment module is further adapted to calculate the user attribute based on the received user inputs.

9. The system of claim 1, wherein the one or more information gathering interfaces includes one or more interactive gaming sessions, wherein the gaming sessions provide challenges or obstacles for the user to overcome and wherein the received user inputs are determined in response to the provided challenges or obstacles.

10. The system of claim 9, wherein the assessment module is further adapted to monitor a user performance during the one or more interactive gaming sessions, wherein the assessment module is further adapted to calculate the user attribute using the user performance.

11. The system of claim 1, further comprising:
a data input module that populates the database by assigning the one or more sector attributes to each of the plurality of sectors based on information obtained from one or more of experts, surveys, and research.

12. The system of claim 1, wherein the user interface module is further adapted to:
present a first stage to the user, wherein the first stage comprises presenting the interactive session to the user;
present a second stage to the user, wherein the second stage is a confirmatory interactive session used to confirm whether the user has aptitude or interest for the identified sector, and the user interface module is further adapted to present a virtual world simulation providing user interaction, and wherein the virtual world simulation is associated with the identified sector.

13. The system of claim 12, wherein the user interface module is further adapted to:
receive user inputs to practice the identified sector by the user in the virtual world and to create an avatar representing the user to practice the identified sector.

14. The system of claim 12, wherein the assessment module is further adapted to:
determine a verified attribute for the user based on the user interaction in the second stage;
perform a reverse comparison in the database using the identified sector to identify an attribute associated with the identified sector; and
confirm that the user has aptitude or interest for the identified sector based on the verified attribute and the identified attribute from the database.

15. The system of claim 14, wherein the assessment module is further adapted to:
compare the verified attribute with the identified attribute; and
provide identification of the identified sector to the user if the verified attribute matches the identified attribute, wherein the match confirms that the user has aptitude or interest for the identified sector.

16. The system of claim 14, wherein the assessment module is further adapted to:
compare the verified attribute with the identified attribute; and
provide an indication to the user that the user does not have aptitude or interest for the identified sector if the verified attribute does not match the identified attribute.

17. The system of claim 16, wherein the assessment module is further adapted to:
perform another comparison in the database using the verified attribute to identify a revised sector if the verified attribute does not match the identified attribute; and
retrieve the revised sector.

18. The system of claim 17, wherein the user interface module is further adapted to:
present another second stage to the user, wherein the another second stage is used to confirm whether the user has aptitude or interest for the revised sector, wherein the another second stage presents another virtual world simulation providing user interaction, and wherein the another virtual world simulation is associated with the revised sector.

19. The system of claim 12, wherein the assessment module is further adapted to:
determine a verified attribute for the user based on the user interaction in the second stage;
compare the verified attribute with the user attribute;
provide identification of the identified sector to the user if the verified attribute matches the user attribute, wherein the match confirms that the user has aptitude or interest for the identified sector; and
perform another comparison in the database using the verified attribute to identify a revised sector if the verified attribute does not match the user attribute.

20. The system of claim 1, wherein the user interface module is further adapted to:
provide a sliding scale input interface to receive enjoyment information from the user relating to the interactive session.

* * * * *